United States Patent [19]
Schneider et al.

[11] Patent Number: 5,647,364
[45] Date of Patent: *Jul. 15, 1997

[54] ULTRASONIC BIOMETRIC IMAGING AND IDENTITY VERIFICATION SYSTEM

[75] Inventors: John K. Schneider, Snyder, N.Y.; Gerald F Marshall, Morgan Hill, Calif.; Andrew D. Vassallo, Williamsville, N.Y.

[73] Assignee: Ultra-Scan Corporation, Amherst, N.Y.

[*] Notice: The term of this patent shall not extend beyond the expiration date of Pat. No. 5,456,256.

[21] Appl. No.: 389,104

[22] Filed: Feb. 15, 1995

[51] Int. Cl.$^6$ ............................................. A61B 8/00
[52] U.S. Cl. ................................................ 128/660.09
[58] Field of Search ..................... 128/660.07, 660.08, 128/660.09, 660.1, 662.03; 73/618–621, 633

[56] References Cited

U.S. PATENT DOCUMENTS

| | | | |
|---|---|---|---|
| 4,034,744 | 7/1977 | Goldbury | 128/660.09 |
| 4,282,880 | 8/1981 | Gardineer et al. | 128/915 |
| 4,385,831 | 5/1983 | Ruell | 356/71 |
| 4,567,895 | 2/1986 | Putzke | 73/639 |
| 4,637,256 | 1/1987 | Sugiyama et al. | 73/633 |
| 4,784,148 | 11/1988 | Dow et al. | 128/660.1 |
| 4,977,601 | 12/1990 | Bicz | 382/4 |
| 5,224,174 | 6/1993 | Schneider et al. | 382/5 |
| 5,258,922 | 11/1993 | Grill | 364/506 |
| 5,456,256 | 10/1995 | Schneider et al. | 128/660.09 |

Primary Examiner—Francis Jaworski
Attorney, Agent, or Firm—HodgsOn, Russ, Andrews, Woods & Goodyear LLP

[57] ABSTRACT

An ultrasonic imaging system and method for imaging human or animal tissue having a surface and including a probe comprising a platen for defining the surface in a manner supporting the human or animal tissue for imaging the same, a transducer positioned closely adjacent the supporting platen for providing an output ultrasonic beam directed on the surface so that the size of the beam at its focal point is as small as possible to maximize the resolution of the system an electrically operated motor for moving the transducer in a manner such that the ultrasonic beam is directed in a path along the surface. A fluid-tight housing extends from the tissue-supporting surface and has an interior region containing the transducer and motor which region is filled by an electrically non-conductive fluid having an acoustic impedance substantially equal to that of water and having a viscosity sufficiently low so as not to impede the movement of the transducer. The housing is provided with a bellows for accommodating thermal expansion and contraction of the fluid. In one aspect of the invention, the motor provides oscillatory output motion and the output shaft is coupled to the transducer so that in response to oscillation of the shaft the output ultrasonic beam is directed in the path along the surface. An encoder is mounted on the shaft between the motor and coupling to minimize any distortion in the information provided by the encoder. The coupling is in the form of an elongated arm having a structure of sufficient rigidity so as not to bend or flex during oscillation of the motor shaft while having minimal drag as the arm moves through the fluid.

29 Claims, 19 Drawing Sheets

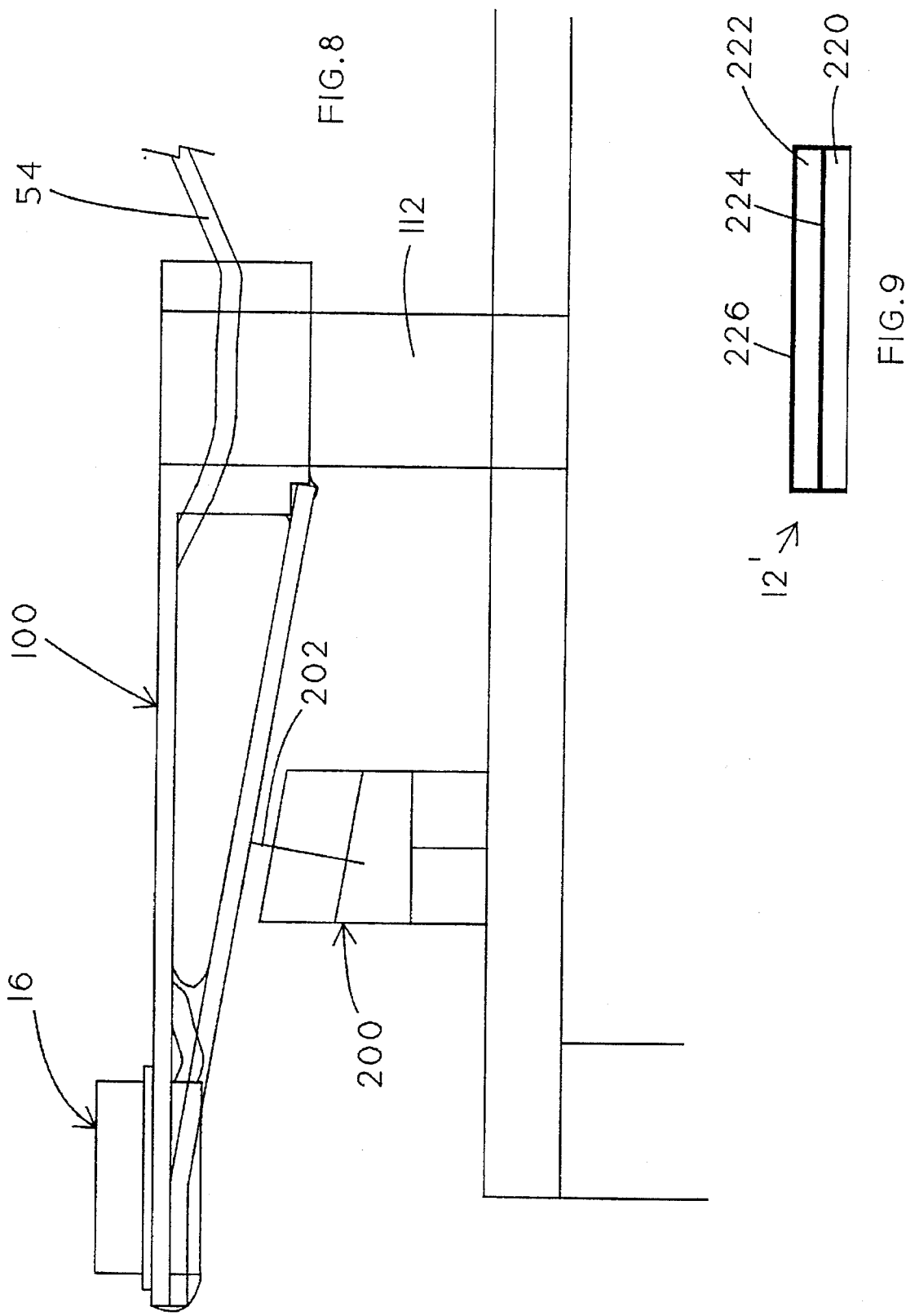

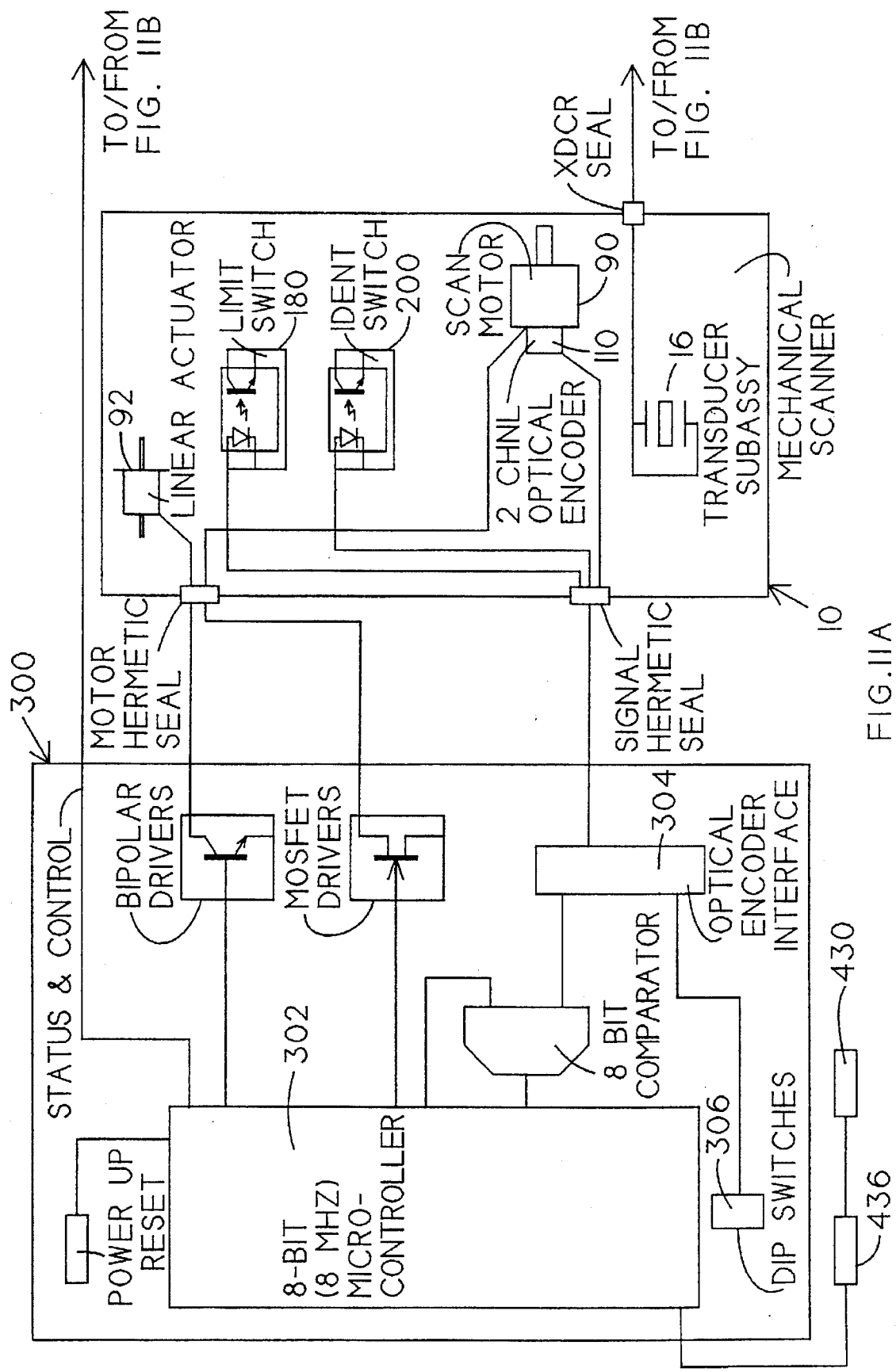
FIG. IIA

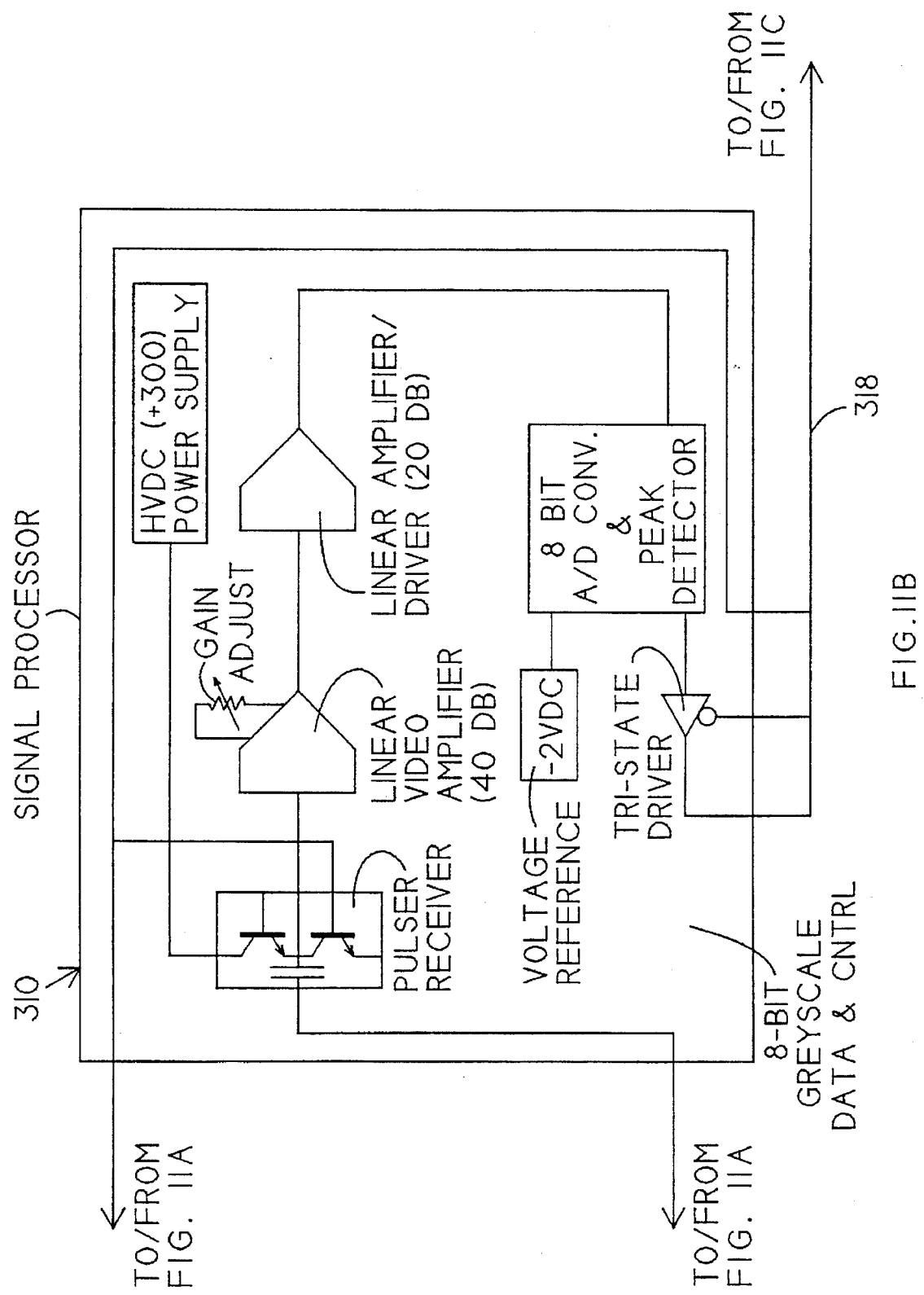

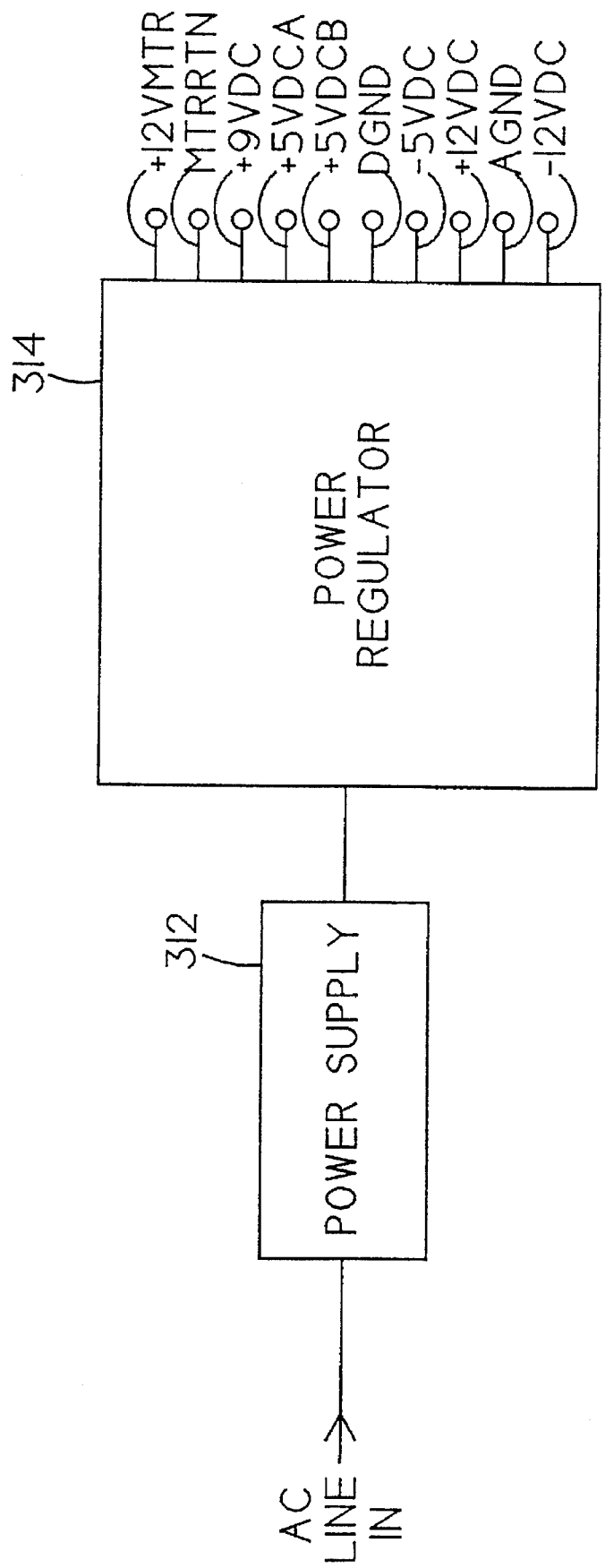
FIG.IID ns. 5,647,364

ULTRASONIC BIOMETRIC IMAGING AND IDENTITY VERIFICATION SYSTEM

BACKGROUND OF THE INVENTION

This invention relates to the art of surface scanning and imaging, and more particularly to a new and improved ultrasonic method and apparatus for surface scanning and imaging.

One area of use of the present invention is in fingerprint scanning and imaging, although the principles of the present invention can be variously applied to scanning and imaging subdermal and other biometric structures. The quality of the images obtained using ultrasound technology is superior as compared to those obtained using optical technology since the ultrasonic images are less dependent on the surface condition of the finger. As a result, by using ultrasound technology, individuals with very dry or very oily fingers, contaminated fingers or fingers having irregular ridge surfaces are able to be imaged equally as well.

In providing an ultrasonic method and apparatus for scanning and imaging fingerprints, subdermal and other biometric structures, there are a number of important considerations. One is obtaining higher quality images which, in turn, requires that the resolution of the system be as high as possible so that the resolution of the resulting images is as high as possible. Another important consideration is improved system performance. One example is performing the scanning as quickly as possible so as to minimize delay and inconvenience and avoid any discomfort to the individual. Related to the foregoing considerations is increased reliability of the system and its operation. Additional important considerations are ease of manufacture and lowering the cost of manufacture.

SUMMARY OF THE INVENTION

It is, therefore, a primary object of this invention to provide a new and improved ultrasonic method and apparatus for imaging human and animal tissue.

It is a more particular object of this invention to provide such a method and apparatus which results in high resolution and high quality images.

It is a further object of this invention to provide such a method and apparatus wherein scanning is performed at a very fast rate.

It is a further object of this invention to provide such a method and apparatus which is highly reliable.

It is a further object of this invention to provide such apparatus which is relatively easy and economical to manufacture.

The present invention provides an ultrasonic imaging system and method for imaging human or animal tissue having a surface and including probe means comprising means for defining the surface in a manner supporting the human or animal tissue for imaging the same, transducer means positioned closely adjacent the supporting means for providing an output ultrasonic beam directed on the surface so that the size of the beam at its focal point is as small as possible to maximize the resolution of the system and electrically operated motive means for moving the transducer means in a manner such that the ultrasonic beam is directed in a path along the surface. A fluid-tight housing means extends from the means defining the tissue-supporting surface and has an interior region containing the transducer means and motive means which region is filled by an electrically non-conductive fluid having an acoustic impedance substantially equal to that of water and having a viscosity sufficiently low so as not to impede the movement of the transducer means. The housing is provided with means for accommodating thermal expansion and contraction of the fluid. In one aspect of the invention, the motive means comprises motor means having an output shaft for providing oscillatory output motion and means for coupling the output shaft to the transducer means so that in response to oscillation of the shaft the output ultrasonic beam is directed in the path along the surface. An encoder means is mounted on the shaft between the motor and coupling means to minimize any distortion in the information provided by the encoder means. The coupling means is in the form of an elongated arm having a structure of sufficient rigidity so as not to bend or flex during oscillation of the motor shaft while having minimal drag as the arm moves through the fluid.

The transducer is oscillated about successive arcuate paths along the area being scanned, and a two dimensional LINEARIZATION process is performed on the data obtained.

In alternative embodiments, the oscillatory output of the motor can be assisted by a flexure spring means, the transducer can be moved by a continuously rotating motor with a slip-ring commutator for making electrical connection to the transducer, and the transducer can be moved linearly in orthogonal directions by the combination of a rotary motor with motion conversion means and a linear actuator.

The scanner of the present invention can be employed in biometric identification and verification systems wherein the imaging system is utilized in combination with a record member containing a recorded biometric image and a processor for performing comparisons.

The foregoing and additional advantages and characterizing features of the present invention will become clearly apparent upon a reading of the ensuing detailed description together with the included drawing wherein.

BRIEF DESCRIPTION OF THE DRAWING FIGURES

FIG. 8 is an enclosed fragmentary elevational view of the coupling arm of the probe of FIG. 1 in relation to an arm position sensor;

FIG. 9 is a diagrammatic view of an alternative form of platen for use in the probe of FIG. 1;

FIGS. 11A, 11B, 11C and 11D are block diagrams of a system containing the probe of FIG. 1;

DETAILED DESCRIPTION OF THE ILLUSTRATED EMBODIMENTS

Figure 1:
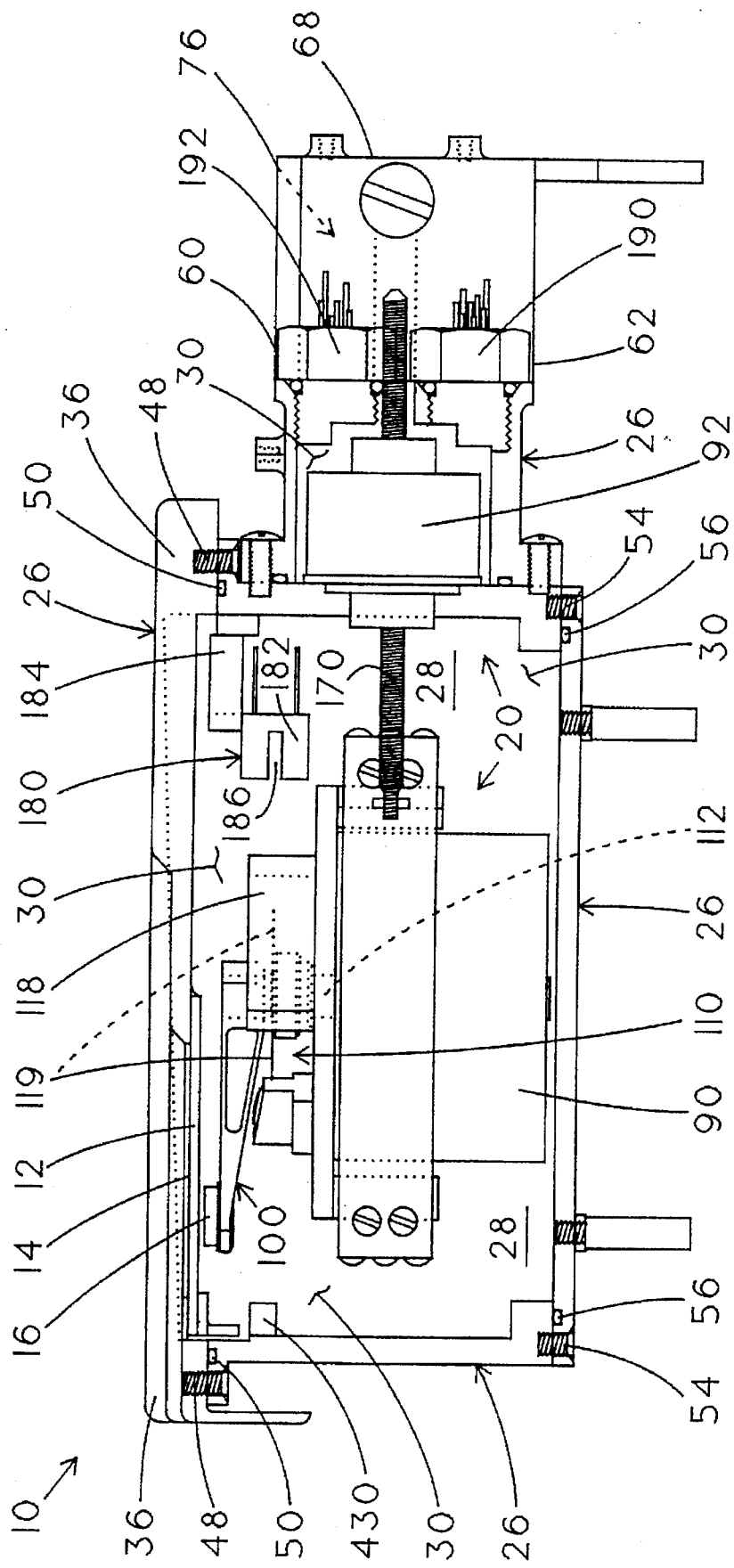
FIG. 1 is a longitudinal sectional view, partly in elevation, of an ultrasonic probe according to the present invention for surface scanning and imaging.

In a basic ultrasonic scanning and imaging system a probe assembly is the part of the system that is responsible for the motion of a transducer in order to obtain a two dimensional scan window, typically having dimensions of 0.75"×0.75" for fingerprint imaging. The motion of probe assembly is controlled by electronics of a scan controller which contains the necessary motor driver logic needed to drive the motors of the probe assembly. The data out of the transducer of the probe assembly is then received by a signal processor where amplification, range gating, peak detection and A/D conversion take place. This data is stored in a high speed data buffer random access memory which is interfaced to any device suitable for receiving and processing the raw fingerprint data. A device such as a general purpose computer or custom fingerprint image processor could be used for this purpose. All of the system components or subassemblies are powered by a power supply which provides the necessary voltages for operating the system.

One of the applications for the technology of the foregoing system is obtaining dermatoglyphics or images of the friction skin surface of the finger, namely the fingerprint. The quality of the images obtained using ultrasound technology over optical technology is superior since these images are less dependant on the surface condition of the finger. This is discussed in detail in U.S. Pat. No. 5,224,174 issued Jun. 29, 1993 and entitled Surface Feature Mapping Using High Resolution C-Scan Ultrasonography, the disclosure of which is hereby incorporated by reference. As a result, individuals with very dry or very oily fingers, contaminated fingers or fingers having irregular ridge surfaces are able to be imaged equally as well. Furthermore, other human and animal tissue surfaces can be scanned, such as palms, toes and the like.

A second fundamental advantage in the use of the ultrasound for fingerprint imaging is using subdermal features that are found within the finger to reproduce the friction skin image. This is useful when the ridge detail on the outer surface of the finger has been temporarily modified such as by small cuts, destroyed altogether, or is not discernible due to excessive wear. The immediate underside of the skin contains all of the detail that the surface friction skin does; therefore, by imaging the immediate underside of the epidermis, a fingerprint image can be obtained free from any defects that might be present on the outer surface of the finger. The second or dermal layer of skin also contains artifacts that correspond to the dermatoglyphics of the friction skin. This layer of skin is composed of structures known as dermal papillae which are arranged in double rows where each row lies in a ridge of the epidermal layer. The only modification in the system previously described that is required to obtain the subdermal images just below the epidermis is to process the ultrasonic signals returned from this depth and not the surface. This is accomplished by adjusting a range gate. The range gate is a window used to allow a particular portion of the return signal to propagate to the signal processing electronics; therefore, delaying the range gate in time corresponds to imaging deeper into the finger.

This technique of subdermal imaging could prove particularly useful for those individuals whose friction skin lacks sufficient detail for analysis. This includes individuals who have undergone some form of trauma to the finger or hand, ranging from the very minor such as small cuts on the surface of the finger to the more severe such as burn victims. This technique would also prove beneficial in imaging others whose occupation tends to wear the ridge structure off from the surface of the finger. Since together these groups of individuals represent a significant percentage of the population, other devices that cannot image below the surface of the finger, such as the optical fingerprint readers, are at a clear performance disadvantage.

A third potential for the application of the technology of the foregoing system lies in the development of an entirely new biometric. It is well known that blood vessel patterns throughout the body have been used as a means of personal identification. Generally, the techniques that must be employed to obtain these images are deemed intrusive by the user and therefore such techniques generally do not succeed in a commercial mass market environment. The system described herein has the capability to penetrate well beneath the surface of the finger and image blood vessels and other subdermal structures. These structures are highly numerous and contain sufficient information to positively identify an individual. An entirely new biometric could be developed with the expectation that this biometric could prove to be much simpler in the post processing necessary to identify an individual using the fingerprint. The simplicity results in higher processing throughputs, greater accuracy, and lower system complexity, which in turn results in reduced system cost.

As previously described, in an ultrasonic scanning and imaging system the probe is the part of the system that is responsible for the motion of the transducer in order to obtain a two dimensional scan window for tissue imaging. In a basic probe arrangement, there is provided a platen for defining a surface in a manner supporting human or animal tissue for imaging the same, a transducer for providing an output ultrasonic beam and positioned closely adjacent the platen, first motive means for moving the transducer to direct the ultrasonic beam along the surface in a first direction and second motive means for moving the transducer to direct the beam along the surface in a second direction. In order to minimize attenuation of the ultrasonic energy as it propagates to the tissue being imaged, the transducer is positioned in a liquid-filled region, i.e. in a water filled cavity. This required, in the foregoing arrangement, establishing a water tight seal in two places on the probe. One seal is a flexible or oscillating seal between the first motive means and the transducer. The second seal is a large bellows responsible for forming the overall liquid cavity. The foregoing basic probe arrangement is shown and described in pending U.S. Pat. No. 5,456,256 issued Oct. 10, 1995 entitled "High Resolution Ultrasonic Imaging Apparatus and Method" and assigned to the assignee of the present invention, the disclosure of which is hereby incorporated by reference.

Thus the basic concept of the foregoing arrangement was that by employing a flexible rubber bellows and oscillating seal, a fluid tight cavity was created. The cavity was filled with water, and the water was contained by the seals, preventing it from contacting the electrically operated motive means which otherwise would cause a short circuit. It is an objective of the present invention to eliminate the two seals, i.e., flexible bellows and oscillating seal, so as to increase the reliability of the probe and simplify its structure and manufacture. This is accomplished according to the present invention by submersing both the motive means or motors in the fluid which, in turn, must be an electrically non-conductive fluid having a low viscosity and acoustic impedance near that of water.

Figure 2:
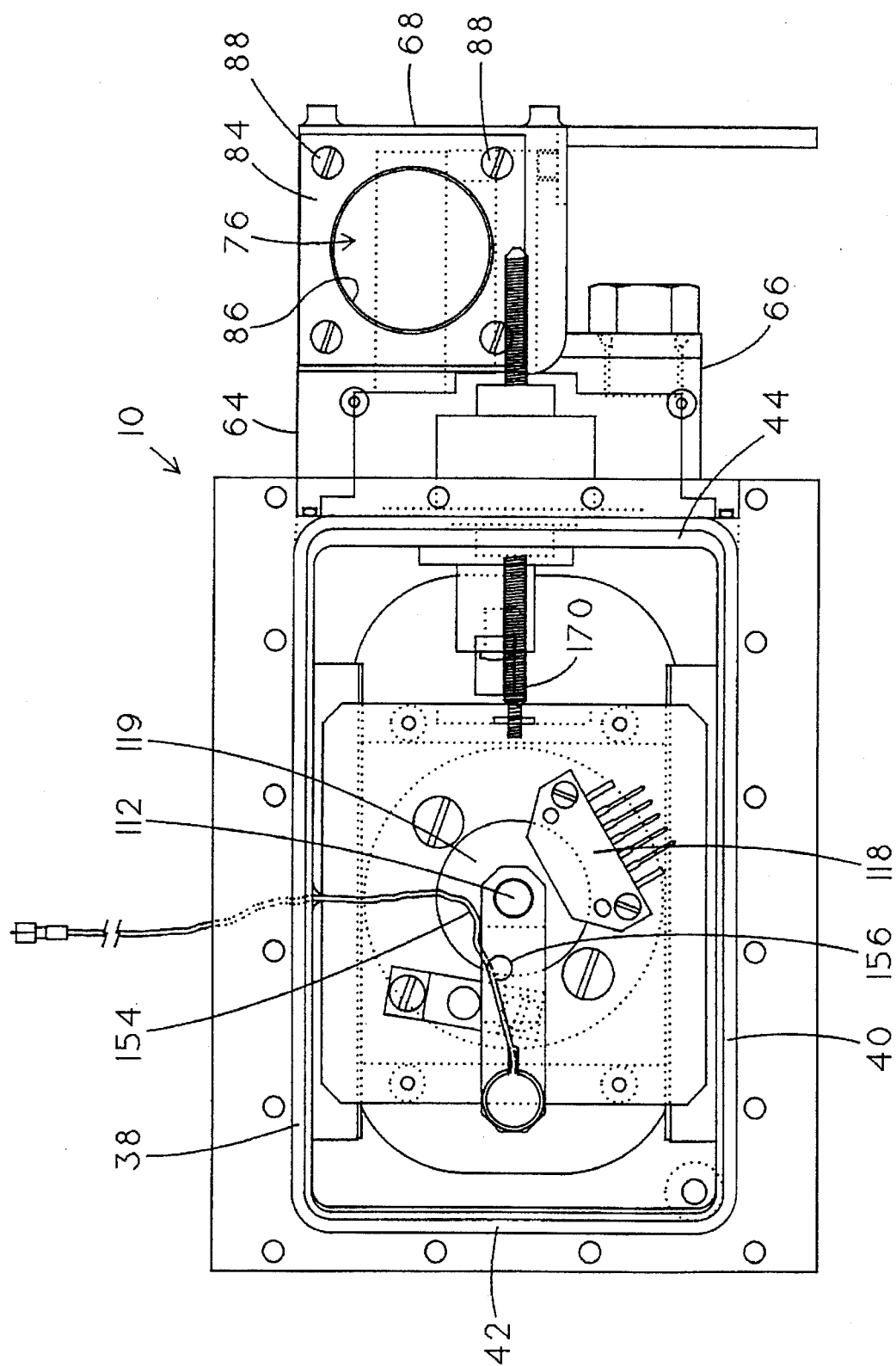
FIG. 2 is a top plan view with parts removed of the probe of FIG. 1.
Figure 3:
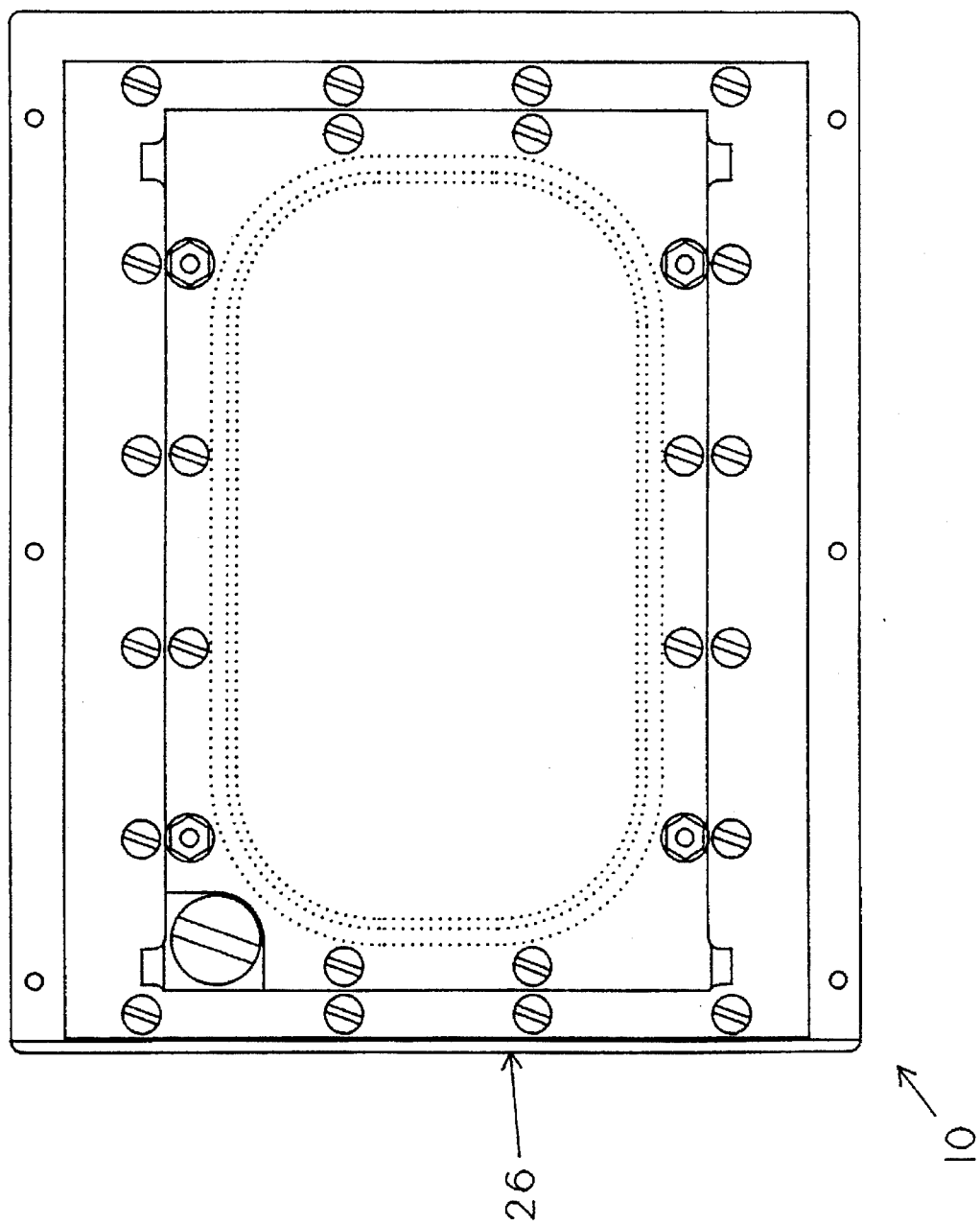
FIG. 3 is a bottom plan view with parts removed of the probe of FIG. 1.

Referring now to FIGS. 1–3 a probe generally designated 10 according to the present invention comprises means in the form of a platen 12 for defining a surface 14 in a manner rigidly supporting human or animal tissue for imaging the same and transducer means 16 for providing an output ultrasonic beam and positioned closely adjacent supporting means 12 in a manner directing, i.e. focusing, the ultrasonic beam on the surface 14 and so that the size of the beam at its focal point is as small as possible to maximize the resolution of the system. There is provided electrically-operated motive means generally designated 20 operatively coupled to transducer means 16 for moving transducer means 16 in a manner such that the output ultrasonic beam is directed in a path along surface 14. The motive means 20 will be described in detail presently.

In accordance with the present invention, there is provided fluid-tight housing means generally designated 26 extending from platen 12 and having an interior region 28 containing transducer means 16 and motive means 20. Also in accordance with the present invention the interior region 28 of housing means 26 is filled with fluid 30. Thus, as can be seen, each of the subassemblies 16 and 20 now reside internal to the sealed cavity 28. This eliminates the need for the oscillating seal and bellows. Eliminating both of these devices removes potential points of failure, increasing system reliability. Furthermore, eliminating these two components simplifies the overall complexity of the mechanical frame and reduces assembly time which results in a cost reduction in manufacture of probe 12.

In order for the subassemblies 16 and 20 to operate submersed in the fluid, a fluid must be selected which is electrically non-conductive. In addition to its non-conductivity, the fluid must also have an acoustic impedance to nearly match that of water so as not to attenuate the high frequency ultrasound. The fluid should have an acoustic phase velocity near that of water so as not to alter the focal length of transducer 16. Another property that the fluid of interest must have is low viscosity so as not to impede the motion of the transducer. It is also important for the fluid to have low air solubility. There are several fluids that meet these requirements and are well known to individuals skilled in the field of ultrasonic imaging. By way of example, in an illustrative probe, fluid 30 is a white petroleum-based mineral oil commercially available from Witco Chemical Corporation under the designation Klearol.

Housing means 26 includes cover assembly 36 which contains platen 12, first and second sidewalls 38 and 40, respectively, extending from cover 36 and joined by a bottom wall 40 and first and second end walls 42 and 44, respectively. The side and end walls are joined to cover assembly 36 by suitable means such as fasteners 48 and a continuous seal or gasket 50 is fitted in a peripheral recess in the joint between the walls and cover to provide a fluid-tight connection. Similarly, bottom wall 40 is joined to the side and end walls by suitable means such as fasteners 54 and a continuous seal or gasket 56 is fitted in a peripheral recess in the joint between bottom wall 40 and the side and end walls to provide a fluid-tight connection. In the probe assembly shown, one of the end walls, in particular end wall 44, carries an extension which is generally hollow rectangular in shape defined by top and bottom walls 60 and 62, respectively, a pair of side walls 64 and 66 and an end cover assembly 68. The extension houses a component of motive means 20 and other probe components which will be described. The interior of the extension is in fluid communication with cavity 28 via openings or passages in end wall 44.

Figure 4:
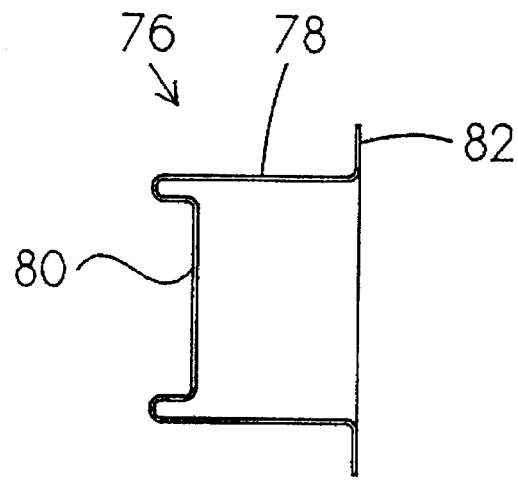
FIG. 4 is a longitudinal sectional view of the expansion bellows in the probe of FIG. 1.
Figure 5:
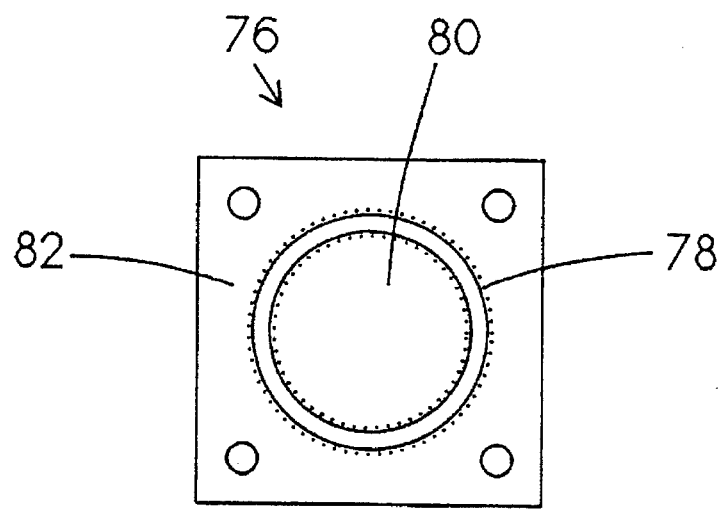
FIG. 5 is an end elevational view, taken from the right as viewed in FIG. 4, of the expansion bellows.

Depending upon the environment to which probe 10 is exposed during transport, storage and use, various ambient temperature conditions will be encountered. Temperature variations of a significant magnitude can cause expansion and contraction of fluid 30. In other words, once the cavity 28 has been filled and purged of all air, it is sealed. As the oil 30 experiences thermal fluctuations due to its surrounding environment, it undergoes thermal expansion and contraction. In accordance with the present invention, housing 26 is provided with means for accommodating thermal expansion and contraction of fluid 30. In the probe apparatus shown, a flexible expansion bellows generally designated 76 is provided in the extension from end wall 44. As shown in FIGS. 4 and 5, bellows 76 comprises a small rubber diaphragm element having a cylindrical wall portion 78 which is closed at one end by a wall 80 and open at the other end which terminates in a peripheral flange 82. As shown in FIG. 2, bellows 76 is mounted in an opening in extension top wall 60 by a mounting plate 84 having a central opening 86 and secured by fasteners 88. The diaphragm or bellows 76 is totally free to move in and out as required. The size of diaphragm 76 is selected to have enough flexibility to accommodate the total thermal expansion experienced for the specified temperature range of probe 10. Diaphragm 76 is made of a neoprene rubber impervious to degradation by the hydrocarbon based oil 30.

Motive means 20 includes first means 90 for moving transducer 16 to direct the ultrasonic beam along the surface 14 in a first direction and second means 92 for moving transducer means 16 to direct the beam along the surface in a second direction. The first direction is into and out of the plane of the paper as viewed in FIG. 1 and the second direction is in the plane of the paper from left to right as viewed in FIG. 1. In the probe assembly shown, the first means 90 comprises motor means for oscillating transducer 16 to move the ultrasonic beam in an arcuate path along surface 14, and the second means 92 comprises motor means for moving transducer 16 to move the ultrasonic beam in a linear path along surface 14. Thus the probe 10 performs a two dimensional scan geometry of the human or animal tissue supported on surface 14.

The transducer 16 is mounted to a probe arm 100 by suitable means such as adhesive, which arm 100 is attached to the shaft of the motor 90 creating an arc to be swept out each time the motor moves through its predefined angle of rotation. The transducer is positioned directly under the platen 12 in which the finger to be imaged is placed. Arm 100 will be described in detail presently.

Once a single line has been scanned, the second motor means 92 in the form of a linear actuator motor is used to move the entire assembly along the second axis of motion, where a second line is scanned. This process is repeated until an equivalent scan area, for example an area of 0.75"×0.75", has been imaged. Upon completing the scan, linear actuator 92 is rewound to its starting position as indicated by a position sensor which will be described in further detail presently.

The probe 10 of the present invention includes position feedback means generally designated 110 operatively associated with motor means 90 in order to provide feedback information to the system control as to the rotational position of motor 90. In the probe shown the position feedback means comprises encoder means. In accordance with the present invention the encoder is mounted on the output shaft 112 of motor 90 between motor 90 and arm 100. Thus, the optical encoder is mounted directly under the probe arm and is immersed entirely in the fluid 30. In this connection, fluid 30 must be optically clear so as not to interfere with performance of encoder 110. The placement of the optical encoder is critical to the overall image quality. In a previous arrangement, the optical encoder was mounted on the shaft of one side of the oscillatory motor and the probe arm was mounted on the other side of the oscillatory motor at the opposite end of the shaft. Thus, any twisting of the shaft over the span was seen directly by the optical encoder. This twisting caused the probe arm to be pointing in one direction while the optical encoder read a different direction. In the probe 10 of the present invention, the encoder 110 is mounted directly under the probe arm 100. This reduces the total shaft length seen between the probe arm and the encoder. As such, the total amount of shaft flex between the two components is minimized. This, in turn, minimizes the amount of registration distortion in the image.

A second improvement to the optical encoder can be found in the mounting technique. Previously, the encoder was mounted using a single set screw tightened onto the motor shaft. This set screw was not strong enough to securely attach the optical encoder to the motor shaft, again resulting in movement of the optical encoder with respect to the probe arm. The new mounting technique employed in probe 10 uses a press fit joint to securely attach the encoder 110 to the shaft 112 of the motor 90. The shaft is knurled prior to mounting the encoder and the encoder is press fit over the knurl. The result is a joint of high integrity several times stronger than the set screw approach.

A third improvement to the optical encoder is increased resolution. Previously, the encoder resolution was 512 lines per revolution. However, due to the increased probe arm length, which will be described, in order to maintain the required resolution for scanning the finger, the resolution of the optical encoder must be increased to 1024 lines per revolution. The angular pixel resolution together with the length of the probe arm results in a scan sample every 0.002".

A fourth improvement in the optical encoder is in the addition of a third channel for absolute position indication. Prior to every scan, the optical encoder electronics needs to be reset. This results in a zero reference indicator to be the current position of the probe arm 100 and optical encoder subassembly. From this position the system software causes the probe arm to scan an angle symmetric around the zero reference. Thus, if the motor 90 does not return to the same position after every scan, the arc which is swept out varies from scan to scan. This results in different areas of the finger to be scanned along with image distortion caused by the bilinearization software which will be described. Adding a third channel to the optical encoder gives an absolute position indication. This absolute position timing mark can be referenced to the zero reference of the optical encoder. Each scan can then be adjusted automatically in software to keep the difference between these two numbers a constant. This results in very repeatable images without any distortion from the bilinearization software.

A fifth improvement relates to the encoder sensor. In a previous configuration, the optical code wheel and the encoder sensor electronics were purchased as a single integrated unit. Deficiencies were found in this arrangement. Specifically, the mounting of the sensor with respect to the code wheel was implemented using plastic. The plastic did not provide a rigid enough mount for the stresses placed on it due to the oscillatory motion of the motor. As such, the electronics would physically move with respect to the code wheel causing extra output pulses. These output pulses were interpreted as Main Bangs and as such, caused extra data points to be captured. This had the net effect of contributing to the line to line misregistration of the image. As a result, the encoder sensor and optical encode wheel are no longer used as an integrated assembly but instead are mounted separately. This ensures that the mounting of the encoder sensor can be done in such a fashion so that it is rigid enough to prevent any movement with respect to the encode wheel. This is accomplished by mounting the sensor 118 onto the aluminum motor base plate 120 in which the motor 90 is mounted. The base plate 120 is much more rigid than the previous plastic mounts and prevents any movement of the sensor 118. The encoder wheel is designated 119 in FIGS. 1 and 2.

By way of example, in an illustrative probe, encoder 110 is commercially available from Hewlett Packard under the designation HEDS-6140 for the codewheel and HEDS-9040 for the encoder sensor 118. The ability of that particular sensor to operate submersed in oil 30 can be enhanced by placing a clear transparent cover over the guarding to encapsulate the LED and lens and prevent oil from coming in contact with the lens.

While the optical encoder was chosen due to its simplicity, ease of use and low cost, other positional feedback devices can be employed. Two which appear to show promise are the capacitive encode wheel and the rotary potentiometer. The capacitive code wheel is simply two plates (electrodes) separated by a small distance. The electrodes are shaped such that the amount of area each electrode overlays the other varies as a function of its rotational position. As such, the overall capacitance varies with respect to rotational position. As in the case of the optical encoder, both absolute and relative encoders are available depending on the electrode deposition pattern. As in the case of the optical encoder, capacitive encoders will also work submersed in oil. The rotary potentiometer is a small, low inertia device that mounts to the motor shaft and provides a resistance output as a function of angular position. The rotary potentiometer has many of the attributes of optical encoders and capacitive encode wheels.

As previously described, transducer 16 is mounted to one end of probe arm 100, the other end of which is attached to shaft 112 of motor 90. The elongated probe arm 100, which is responsible for holding the ultrasonic transducer 16, must be rigid enough to not flex or bend thus causing movement of the ultrasonic beam. Furthermore, it must obtain this rigidity without adding significantly to the cross-sectional area of the probe arm thereby increasing the drag as it moves through the fluid 30. The increase in drag would cause an increase in the load as seen by the oscillatory motor 90 thereby slowing down its scan rate. In accordance with the present invention, probe arm 100 is provided with a structure of sufficient rigidity so as not to bend or flex during oscillation of shaft 112 of motor 90 while having minimal drag as arm 100 moves through fluid 30. In particular, probe arm 100 extends in a direction substantially perpendicular to the longitudinal axis of the motor shaft 112, i.e. extends in a substantially horizontal direction as viewed in FIG. 1, and probe arm 100 comprises a pair of arm sections spaced apart in a direction substantially parallel to the longitudinal axis of motor shaft 112, i.e. vertically spaced apart as viewed in FIG. 1, so that probe arm 100 has sufficient rigidity so as not to bend or flex during oscillation of motor shaft 112. In addition, the arm sections have surfaces disposed in planes substantially parallel to the longitudinal axis of motor shaft 112, i.e. in substantially vertical planes as viewed in FIG. 1, which surfaces have a sufficiently small area so as to minimize drag as probe arm 100 moves through the fluid. Thus, those surfaces of the arm sections define a biplanar probe arm structure.

Figure 6:
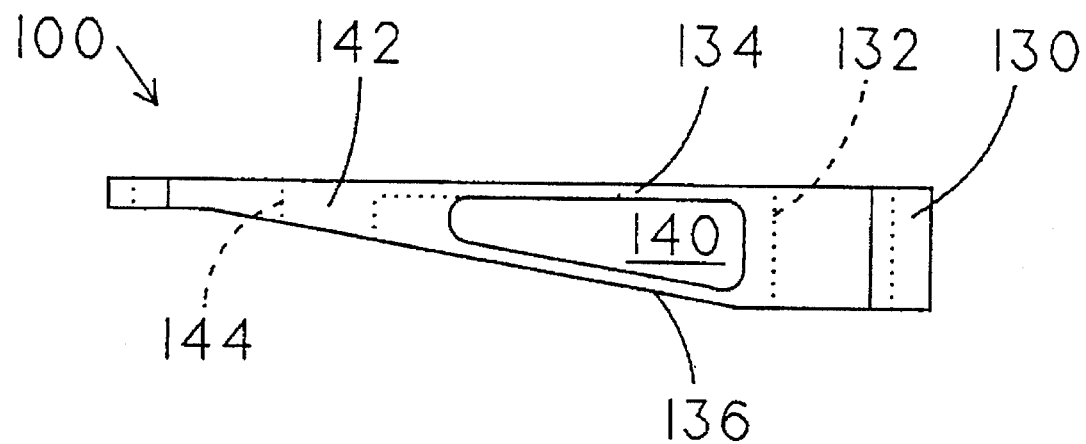
FIG. 6 is a side elevational view of the coupling arm of the probe of FIG. 1.
Figure 7:
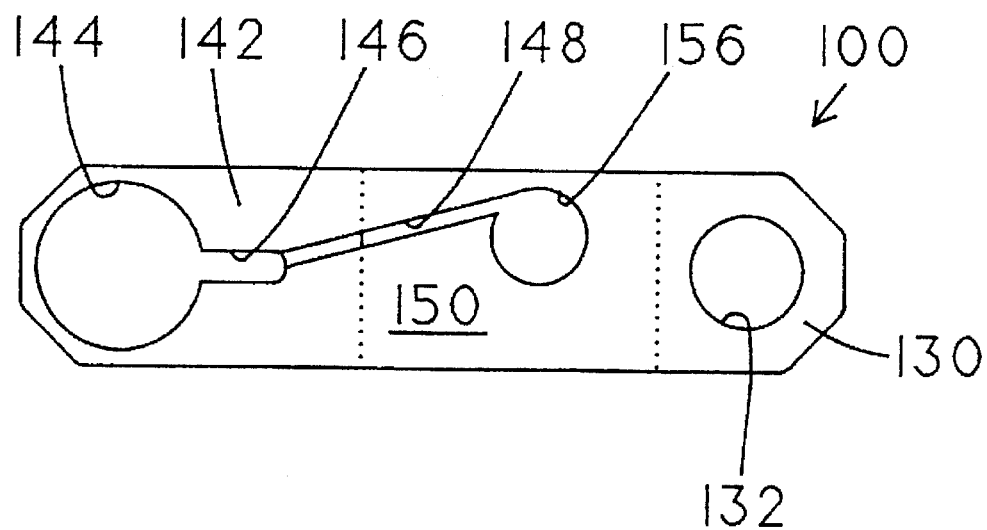
FIG. 7 is a top plan view of the arm of FIG. 6.

Referring to FIGS. 1, 6 and 7, probe arm 100 includes a body portion 130 at one end provided with a through bore or aperture 132 for mounting arm 100 onto the output shaft 112 of motor 90. Probe arm 100 further includes a first arm section 134 extending outwardly from the upper end of body 130 as viewed in FIGS. 1 and 6 in a direction generally perpendicular to the longitudinal axis of bore 132 and a second arm section 136 extending outwardly from the lower end of body 130 at an angle to the axis of bore 132 which defines an acute angle with respect to arm section 134. As a result, the converging arm sections 134, 136 define an open region or space 140 therebetween and meet to define a solid body portion 142 at the opposite end of probe arm 100. A through bore or aperture 144 is provided in body portion 142 to receive transducer 16 which is fixed therein. A first slot 146 extends inwardly from bore 144 and joins a second slot 148 formed in the top surface 150 of arm 100 as viewed in FIG. 7 to provide a path for an electrical conductor 154 shown in FIG. 2 extending from transducer 16 along the top surface 150 of arm 100 and through an opening 156 in arm section 134 to external circuitry.

The two probe arm sections 134 and 136 provide a means of strengthening probe arm 100 while adding minimal drag while moving through fluid 30. As compared to a probe arm having a single section of a thickness equal to the sum of the thickness of arm sections 134, 136, the biplanar probe arm 100 of the present invention provides a significant increase in overall rigidity while keeping the total drag and inertia the same.

In the probe 10 shown in FIGS. 1 and 2, the motor of the transducer 16 is oscillatory with an angle of oscillation of approximately ±20°. Although conventional brushless DC motors can be controlled to provide this motion, they are more complex than is really needed and as such are more expensive. This complexity also carries over to the control electronics. Therefore, an oscillatory motor (a motor with limited angular rotation) was selected for the motor 98 to move the transducer 16 back and forth. These devices, often referred to as rotary solenoids or brushless torque actuators, are very simple, low cost, and can generate very high torques which in turn can move the transducer 16 faster. Furthermore, the control electronics is simplified by not requiring the sophisticated hall effect sensor interface logic that is needed for conventional brushless DC motors. By way of example, in an illustrative probe 10, motor 90 is a brushless torque actuator commercially available from Lucas Control System Products of Vandalia, Ohio.

Once the first motor means or oscillatory motor 90 has swept transducer 16 across a singular line representing a path of the ultrasonic beam along surface 14, the second motor means 92 is operated to step the assembly of transducer 16, arm 100 and motor 90 along a linear path which is the second axis of scanning. Motor means 92 is a linear actuator comprising a small DC stepper motor with an integral lead screw 170 attached so as to convert rotational motion into linear motion. Once the system control has sensed that the transducer 16 has completed a line scan, the linear actuator 92 is commanded to move along the second axis of motion by a single line. The motion of transducer 16 is then reversed to sweep the ultrasonic scan back across the surface 14 in the opposite direction. This process is repeated until the desired area has been scanned. The linear actuator 92 is then rewound to its starting position in preparation for a new scan. A Sensor, which will be described, provides positional feedback to indicate that the linear actuator 92 has rewound to the starting position and provides a signal to the system control to halt the rewind process. By way of example, in an illustrative probe, linear actuator 92 is commercially available from Hayden Switch Instruments under model number 35862.

In the probe 10 shown in FIGS. 1 and 2 during a preferred mode of scanning as described hereinabove, linear actuator 92 advances screw 170 to move the assembly of transducer 16, arm 100 and motor 90 to the left as viewed in FIGS. 1 and 2. When the scanning of a finger or other tissue is completed the assembly will be at its extreme left-ward position where linear actuator 92 rotates screw 170 in the reverse or rewind direction. In order to determine when the full return position of the assembly is reached, there is provided position sensing means generally designated 180 responsive to proximity of a detectable component of the assembly for signalling when transducer 16 has moved a predetermined distance along the linear path, i.e. when the full return position of the assembly is reached. Sensing means 180 comprises a photoelectric or optical sensor having a housing 182 fixed to end wall 44 by a bracket 184 and having a recess or open region 186 facing toward the linearly movable assembly and having the optical beam or path therein. Sensor 180 is located so that when the full return position is reached, the periphery of the code wheel of encoder 110 enters recess 186 and breaks the optical path thereby causing an indicating signal. Thus, sensor 180 operates in the manner of a limit switch.

A number of the electrically-operated components of probe 12, including transducer 16, motors 90 and 92, encoder 110 and sensor 118, and limit switch 180 operate fully submersed in the oil 30. As such, the electrical connections for these components are also submersed in the oil. Each electrical connection must therefore be brought out of the oil to its corresponding interface circuitry. To do this, two hermetic seals are used. These seals, designated 190 and 192 in FIG. 1, contain the necessary number of wires to bring all of the power, grounds and signal wires to and from the various electrical components housed within the oil. The only signals not brought out in this fashion are the power, ground and signal associated with the ultrasonic transducer 16. These signals are carried on conductor 154 which is a miniature coaxial cable and sealed separately from the rest of the wires. By way of example, in an illustrative probe, hermetic seals 190 and 192 are of the threaded plug variety commercially available from PAVE Technology Co., Inc. under the designation PAVE-Seal.

As previously described, the addition of a third channel on the optical encode wheel of encoder 110 provides an absolute position indication which is needed for repeatable, high quality images. However, if the diameter of the code wheel is sufficient to increase the load inertia and thereby reduce the scan speed of the oscillatory motor 90, an alternate approach can be employed. This approach uses a conventional 2-channel optical encode wheel and achieves the third channel position indication by an external sensor. This sensor is an infrared LED and photosensor reflectometer designated 200 in FIG. 8. It is positioned directly under the probe arm 100 approximately 10° from center position.

When the probe arm is not over the sensor 200, no reflection of the infrared beam 202 occurs and the photosensor indicates such. When the leading edge of the probe arm 100 covers the sensor, optical reflection occurs and drives a signal for the control electronics. This signal is used to latch in the state of the optical encoder bits to be read and compared to a previously stored count for comparison. As a result, the overall effect is the same as that provided by an integrated third channel on the optical encode wheel without the increase in load inertia. Thus, sensor 200 comprises means spaced from arm 100 and detectably coupled to arm 100 for indicating a reference position of the arm.

The supporting means or platen 12 creates the interface between the finger and fluid path of the ultrasonic transducer 16. If must be of sufficient mechanical strength to provide a rigid support for the finger during the scan process. Deflection or deformation of the platen 12 could result in a distorted image and make the post processing software more difficult. Ideally, the acoustic impedance of the platen 12 must match the skin of the finger as close as possible. Furthermore, since it is highly desirable to place a finger onto the platen 12 without the use of any types of acoustic coupling, the platen interface must be able to fully contact the surface of the finger, minimizing any air gaps in-between. All of these requirements coupled with the ability of the platen 12 to pass high frequency ultrasound without without appreciable attenuation or frequency down shift must be met in order to obtain high quality images of the finger.

Platen 12 is constructed using a cross-linked polystyrene or perspex material coated with a thin layer of silicone RTV. The body of polystyrene or perspex material has an acoustic impedance very near that of human tissue and a thickness suitable to provide the necessary mechanical rigidity and provide as short an ultrasonic path as possible, for example a thickness in the range of 1/16 inch to 1/8 inch. Ultrasonic frequencies of 30 MHz are able to propagate through the material without appreciable modification. In order to provide maximum coupling to the finger, if desired the platen 12 can be coated on the external surface contacted by the tissue being image with the thin layer of silicone RTV. Other types of silicone latex rubber can be employed. The RTV improves the mechanical coupling to the finger while maintaining the proper acoustic impedance. The RTV must be of sufficient thickness so as to be able to range gate out the polystyrene/ RTV return echoes and process only those echoes associated with the RTV/finger interface. The required thickness of RTV is dependent upon the overall "Q" of the transducer 16. By way of example, in an illustrative system, the platen body has a thickness of about 1/16 inch to 1/8 inch and the coating has a nominal thickness of about 0.010–0.030 inch.

Platen 12 is sealed in cover 36 thereby maintaining the fluid-tight integrity of the probe structure. The outer surface of platen 12 can be subject to wear over a period of time thereby requiring field replaceability of platen 12. These two requirements can be satisfied by a two piece platen 12' as shown in FIG. 9 comprising a first or inner layer 220 which is permanently sealed to cover 36 and maintains the fluid-tight integrity of the probe structure. A second or outer platen layer 222 is coupled to the first layer by an acoustic gel 224 or the like and is easily removable for replacement. The outer surface of layer 222, which is contacted by the tissued being imaged, can be provided with a coating 226 like the silicone RTV coating previously described.

Two forms of transducer 16 can be employed depending upon the type of scanning. A high frequency transducer of approximately 30 MHz, with an aperture of approximately 0.180" and a focal length of approximately 0.25" can be used for fingerprint imaging. This transducer provided the highest resolution, i.e., smallest spot size, but was not significantly attenuated due to the limited depth of penetration into the finger. A second transducer of similar physical characteristics but reduced in frequency to approximately 15 MHz can be used for the subdermal scanning that was targeted at artifacts other than the fingerprint structure. For this imaging, the 30 MHz ultrasound would be so significantly attenuated that the cost of the signal processing electronics would be prohibitive. Therefore, by dropping in frequency by a factor of 2, a much stronger signal is received.

A principal requirement on transducer 16 is to minimize the overall spot size which it generates. The spot size is a function of the frequency of the transducer, aperture and overall focal length and is given by:

$$d = 2.44(f_L/D)\lambda$$

where d is the spot size measured at the zero crossing points, $f_L$ is the transducer focal length, D is the transducer aperture and $\lambda$ is the wavelength of the soundwave. In the design of a transducer, it is desired to keep the ratio $f_L/D$ as small as possible. This can be accomplished using a variety of well-known techniques such as an external focusing lens, a curved transducer element or a combination of both. By way of example, in an illustrative system, transducer 34 produces a spot size of 0.002 inch measured at—6 db points per ASTME1065 and has a ring time of 1 cycle measured at—20 db down from peak. Cable 154 is Cooner coaxial or the equivalent having a diameter of about 0.037 inch. An illustrative commercial form of transducer 34 is available from Krautkramer Bransen under model no. 389-005-860.

As previously described, a typical scan area of surface 14 has dimensions of 0.75 inch by 0.75 inch. There are some applications, such as NCIC 2000 law enforcement initiated by the F.B.I. that call for larger scan areas up to a maximum of 0.88"×122'. The scan geometry of the probe 12 of the present invention meets the increased area requirements. In order to do this, several components need to be changed. To increase the scan length (y-axis) from 0.75" to 1.22", the linear actuator 92 must be stepped an additional 235 steps (0.002"/step). The linear actuator 92 has sufficient travel and thus requires only a software change to the control electronics. To increase the scan width from 0.75" to 0.88" (the x-axis), several components need to be changed. It was determined that rather than drive the oscillatory motor 90 at a larger angle, the length of the probe arm 100 should be increased. Thus for the same angle of sweep, larger segments can be scanned. In fact, an optimum probe arm length of 1.3" is used. This in turn requires a scan angle of ±21.3°. The reduced scan angle has the added benefit of increasing the scan frequency thereby reducing the overall scan time. As a result of the reduced scan angle, faster more efficient forms of oscillatory motor could be used for the oscillatory motion. The increase in probe arm length to 1.3" requires a change in the resolution of the optical encoder 110 in order to sample at the required spatial frequency. The optical encoder 110 was increased from 512 lines per revolution to 1024 lines per revolution. This resolution in code wheel 119 coupled with the circuitry of decoder 118 results in a angular resolution of 0.087°. This maps to a linear scan resolution of one sample per 0.002".

Due to the arc-scanning motion of the ultrasonic transducer 16, data is collected in a non-linear fashion along this axis, i.e. the x-axis. Specifically, the data is not collected line by line but rather arc by arc. In addition, the amount of distance swept out between pixels near the center of the scan varies from the edges of the scan. As a result, this skew or distortion must be corrected. This correction is a mapping of pixels in one geometric space to pixels in another geometric space. Naturally, this mapping is not a one to one mapping. The pixel to be placed in the corrected geometric space is often from a point between pixels of the original geometric space. As such, the data values or grey scale values must be determined. Therefore, in effect, two axes of linearization are taking place, hence the name bilinearization. The first correction is the placement of pixels from the input geometric space to the output geometric space. The second correction is the determination of what grey scale value is to be used.

With respect to the mapping of the input geometric space to the output geometric space, this is nothing more than a simple table lookup method. The values in the table are determined according to the following method. The first step is to find the actual coordinates of each scanned pixel along the scan arc. Assume, for example, pixel number 256 is located at a scan angle of 0° along the arc.

$$\theta_{256}=0°$$

$$X_{256}=0.750(\text{inch}) \sin 0°$$

$$Y_{256}=0.750(\text{inch}) \cos 0°$$

where 0.750 inch is the length of the scan arc previously described. Pixels on either side are offset with respect to pixel 256. Thus, $$\theta_{255}=(255-256)(90°/512)$$

$$X_{255}=0.750(\text{inch}) \sin (-0.1758°)$$

$$Y_{255}=0.750(\text{inch}) \cos (-0.1758°)$$

$$\theta_{257}=(257-256)(90°/512)$$

$$X_{257}=0.750(\text{inch}) \sin (-0.1758°)$$

$$Y_{257}=0.750(\text{inch}) \cos (-0.1758°)$$

where 512 is the encoder resolution of 512 lines per revolution.

The next step is to change the foregoing actual coordinates into pixel coordinates by dividing by 0.002 inch since a scan sample is taken every 0.002 inch.

$$X_{255}=X_{255}/0.002=-1.15$$

$$Y_{255}=Y_{255}/0.002=375$$

$$X_{256}=X_{256}/0.002=0$$

$$Y_{256}=Y_{256}/0.002=375$$

Then the middle pixel #256 is centered at location 256 by shifting all X coordinates by +256.

$$X_{255}=-1.15+256=254.85$$

$$X_{256}=0+256=256.00$$

The next step is to shift the Y coordinates by −265.15 (make Y=0 at a scan angle of 45°);

$$0.750(\text{inch}) \cos 45°/0.002\text{inch}=265.15$$

$$Y_{255}=375-265.15=109.85$$

$$Y_{256}=375-265.15=109.85$$

Finally, for each new line scanned, Y positions are offset +1 from the last line due to the linear movement of 0.002 inch per line.

line 1: $Y_{250}=109.85$ line 2: $Y_{250}=110.85$ line 3: $Y_{250}=111.85$ etc.

Thus, the table look up values for the mapping of the input geometric space to the output geometric space are obtained according to the foregoing method.

Regarding the selection of the proper grey scale value, this can be accomplished by taking a weighted average from the surrounding four data points. This process is given by the following equation:

$$\ell(i,j)=(1-i')\{j'\ell(i,j+1)+(1-j')\ell(i,j)\}+\{j'\ell(i+1,j+1)+(1-j')\ell(i+1,j)\}$$

where i,j=input image data point i',j'=output image data point

Figure 10:
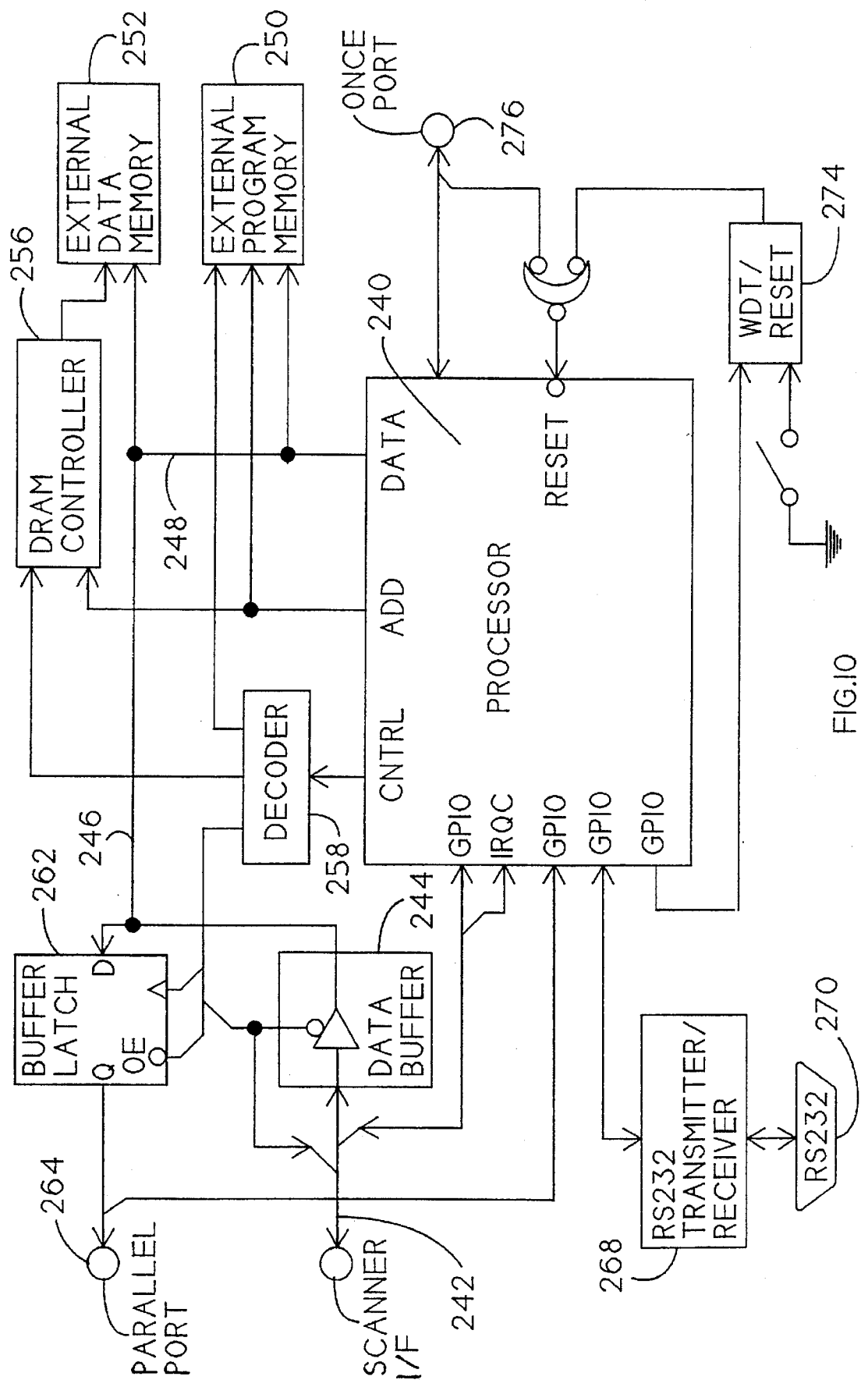
FIG. 10 is a block diagram of a bilinearization processor for use in conjunction with the probe of FIG. 1.

In order to make this mapping in real time, a high speed DSP chip is used. This processor collects the data line by line and maps it to the proper output while correcting its greyscale amplitude. This is done in real time and is overlapped with the scan time of the scanner itself, thereby causing minimal throughput delays. A block diagram of the Bi-Linearization processor is given in FIG. 10.

The processor is centered around a DSP chip 240 which, by way of example, can be a Motorola 56166 processor. Incoming data from the scanner on line 242 is interfaced by a data buffer 244 and is sent to processor 240 via the bi-directional data busses 246 and 248. A permanent memory or flash PROM 250 stores the program used by the processor 240. A dynamic RAM or external memory 252 stores data for use by processor 240. The bi-directional data bus 248 is connected to both memories 250 and 252. A controller 256 is provided for DRAM 252, and a decoder 258 is associated with the control of processor 240. Processed data from chip 240 is transmitted over the bi-directional data busses 248 and 246 to a buffer/latch 262 which interfaces with a parallel part 264 of the system computer. Processor 240 is connected via a level translator 268 to a serial part 270 of the system computer. A watchdog timer 274 and a debugging part 276 also are associated with processor 240 in the manner shown.

Turning now to the various modes of scanning, acquiring images from the surface of the finger or near the surface of the finger such as in the case of subdermal fingerprint imaging, the amount of attenuation of the ultrasonic signal is minimum. Therefore, in order to obtain maximum spatial resolution, the frequency of the transducer 16 is very high. For this application, the frequency of the transducer is approximately 30 Mhz. In order to capture images from structures just below the surface of the finger, an electronic range Sate is used to allow only those echoes returned from the depth of interest to be processed. Therefore, the only modification to the system to process surface fingerprint images versus subdermal fingerprint images is in the application of the range gate. The timing of this range gate can be controlled by software making it a transparent change to the person that is being imaged.

In both cased the ultrasonic energy enters the finger at a 90 degree angle to the surface of the finger. Orienting the transducer 16 in this fashion gives the maximum signal strength possible. However, the specular reflections from the front and back sides, respectively, of the platen 12 are also returned to the transducer 16. This is not a problem for surface imaging since they can be range gated out. However, for deep subdermal imaging, the multipath specular reflections can represent a severe problem when trying to image at particular depths. Therefore, the transducer 16 must be oriented in such a way as to eliminate these echoes.

When images from deeper in the finger are of interest, the amount of attenuation of high frequency ultrasonic signals is so significant that either the signal is lost altogether or the gain bandwidth product of the amplification stages found in the system signal processor become so large that the cost of the system is prohibitive. Therefore for imaging these structures, a lower frequency transducer 16 is used, for example at 15 Mhz. This solves the problem of high attenuation at the cost of slightly reduced spatial resolution. However, the loss of resolution is not critical since the subdermal structures of interest are larger than the ridge structures found on the surface of the finger.

A secondary problem that can occur when imaging deep inside the finger is that depending on the depth at which the echo is to be collected, a multipath echo from specular reflectors that fall in the path of the sound wave may shadow the artifact of interest. Therefore, the multipath echoes that are caused by the specular reflectors need to be removed so as to enable imaging of the actual signals of interest. This can be accomplished by rotating the transducer 16 off axis by a small number of degrees sufficient to cause the specular return echoes to be missed. This causes any echoes due to a smooth surface to reflect at an angle such that the return echo never makes it back to the transducer 16. Only those echoes that scatter the sound wave in all directions can be seen by the transducer 16. Most structures of interest internal to the body will tend to scatter the soundwave, thereby making this technique very effective for this scanning application.

The industry standard for fabricating lenses for focusing ultrasound is to use a fixed radius to create the curvature of the lens. The lens material is normally made from polystyrene and is machined down to the desired size and curvature. This geometry is responsible for defining the focal length of the transducer and the spot size. However, analysis of the lens equation readily shows that constant radius lenses do not provide a diffraction limited spot size. They cause spherical aberrations which have the effect of blurring or enlarging the size of the focused beam. Therefore, in order to reduce the size of the spot to the theoretical minimum, a non-spherical shaped lens, a curved transducer element or a combination of a curved element and non-spherical lens must be employed.

Figure 11C:
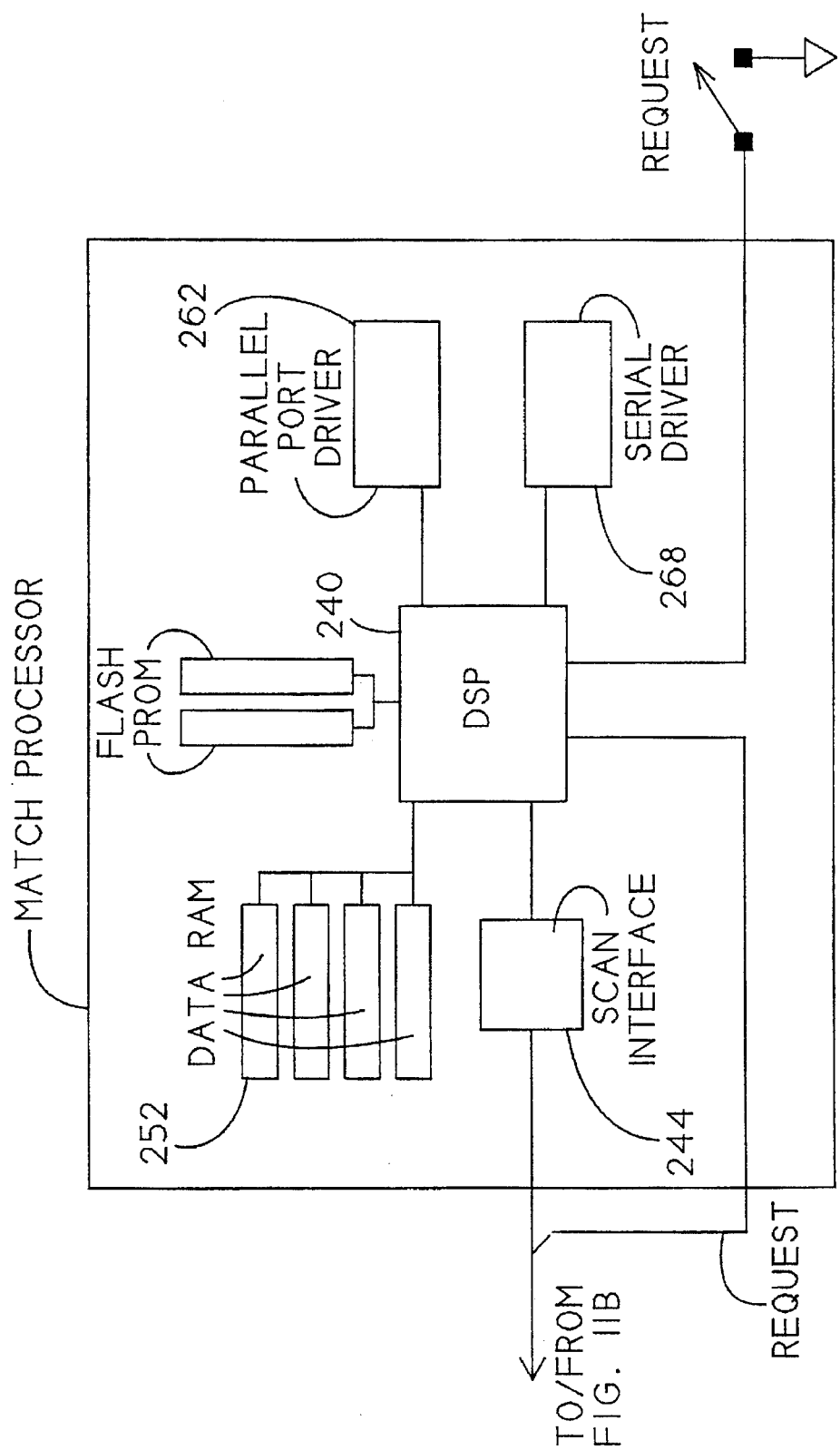

FIG. 11A is a block diagram of an ultrasonic imaging system of which probe 10 is a part. The motion of the probe or mechanical scanner 10 is controlled by torque controller 300 which includes a micro-controller 302, optical encoder interface 304 and angle correction switches 306 which will be described. A signal processor 310 energizes transducer 16 and data from transducer 16 is received by signal processor 16 where amplification, range gating, peak detection and A/D conversion take place. Voltages for operating the system are obtained from a power supply 312 and regulator 314. The bilinearization processor of FIG. 11B is connected to signal processor 310 via bus 318. It stores data and also corrects for any geometric distortion caused by the arc scanning motion.

Torque controller 300 functions to ensure that the scan of oscillatory motor 90 is consistent in its absolute position from scan to scan. The scanner 10 at the time of assembly is calibrated. This calibration is to move the probe arm 100 from its center position until the third channel (IDENT) marker fires. The IDENT marker can be implemented either as the third channel of the optical encoder 110 or by the external arc limit switch 200. Once this fires, the output of the optical encoder 110 is read. This output represents the total angle or distance the absolute IDENT marker is from zero position. This value is now entered onto an angle correction or DIP switch 306 located on the torque controller 300.

During normal operation, the motor 90 comes to rest at a slightly different spot at the end of every scan. It does not consistently return to the zero position. As a result, the final resting spot of the motor 90 would become the zero position for the next scan. As such, the position of each scan would vary from scan to scan. In the improved implementation provided by torque controller 300, at the beginning of each scan the motor 90 is oscillated momentarily without the finger being imaged. During this time, the output of the optical encoder 110 is read by the torque controller 300 at the firing of the IDENT signal. The value seen here should match the value stored on the DIP switches 300 which were previously set at the time of calibration. Thus, the torque controller 300 reads the DIP switches 306 and does a comparison. If the values do not match, the torque controller software adjusts the scan angle an amount equal to the difference between the switch setting and the actual read value. Doing such, ensures that the scan will be perfectly centered every time resulting in very consistent images.

FIGS. 12–16 illustrate alternate architectures which address the issue of providing the highest possible scan speed while providing the smoothest and quietest operation of the scanning device. In the probe 10 of FIGS. 1–8, the transducer 16 is moved in an oscillatory fashion by a brushless torque actuator 90. The mass of the transducer 16, its distance from the point of rotation and its hydrodynamic drag in the oil 30 all add to the inertial load of the system. This load is sufficient enough to put tremendous torque requirements on the actuator 90. The torque requirements are high enough to impose limits on the speed at which brushless torque actuators can drive the probe arm assembly. Therefore, in accordance with the present invention, in order to assist the oscillatory motion of the motor 90, an external spring can be added. One type of spring, known as the flexural bearing, is particularly suited for this application. It is a spring which is designed to flex in both directions and when properly designed, will have infinite life.

Figure 12:
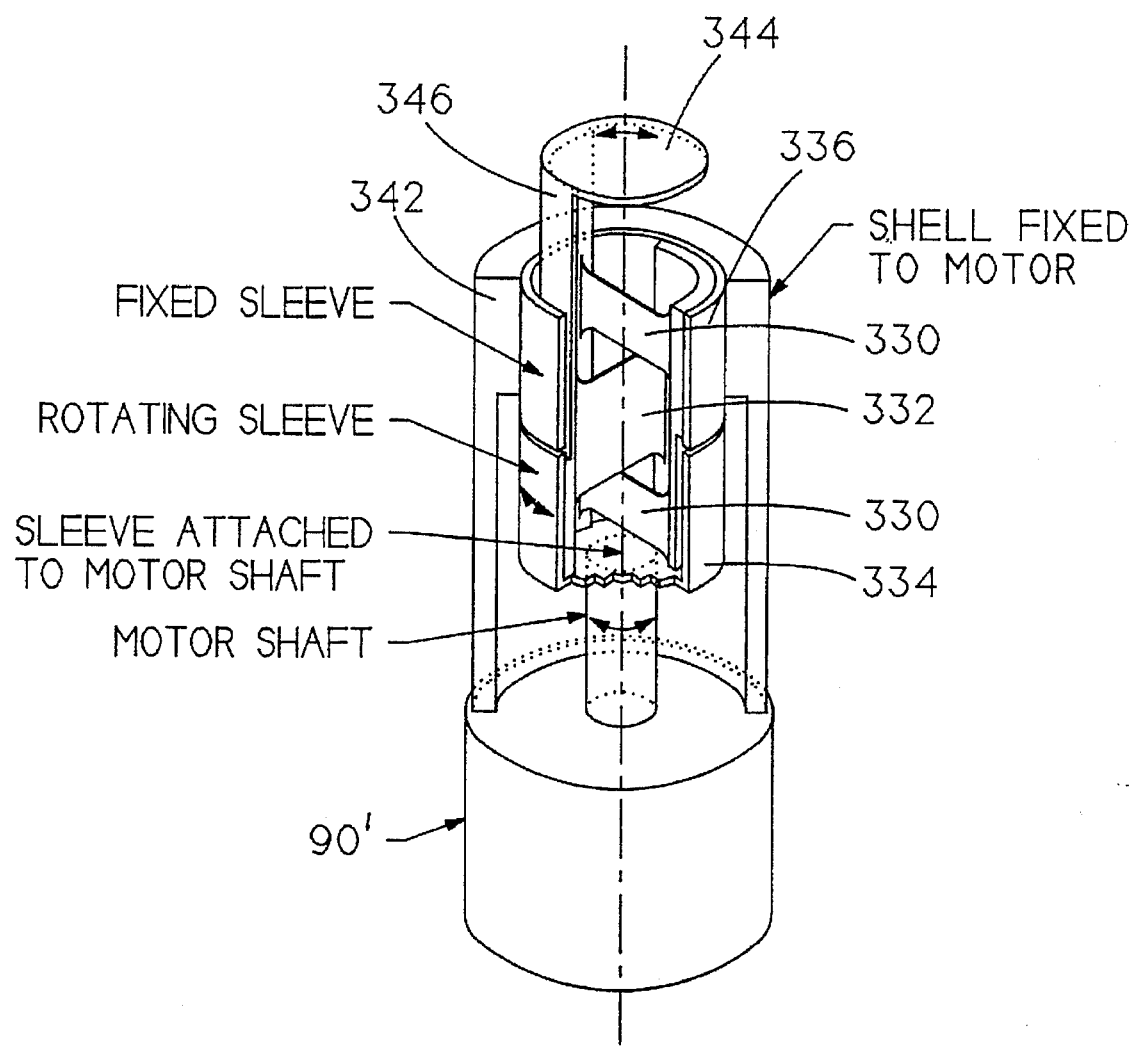
FIGS. 12, 13, 14A, 14B, 15 and 16 are diagrammatic views of alternative architectures for moving the transducer during scanning in a probe of the type shown in FIG. 1.

FIG. 12 shows one form of spring means operatively associated with motor 90' to assist the oscillatory motion of the motor. The spring means or flexual bearing means is mounted external to motor 90' and is the simplest of configurations requiring no rework to the motor 90'. As shown in FIG. 12, the flexual bearing means comprises flat, crossed springs 330, 332 supporting rotating sleeves 334, 336. One of the flexual bearing sleeves 334 is attached by a member 340 to the motor output shaft 112'. The other of the flexual bearing sleeves 336 is attached to a shell 342 fixed to the housing of motor 90'. An output coupling in the form of a disc 344 is connected by a member 346 to the movable bearing sleeve 334. Disc 344, in turn, would be fixed to the end of the probe arm which carries the transducer at the other end. The arrangement of FIG. 12 provides scan frequencies significantly greater than those obtained with the motor alone.

Figure 13:
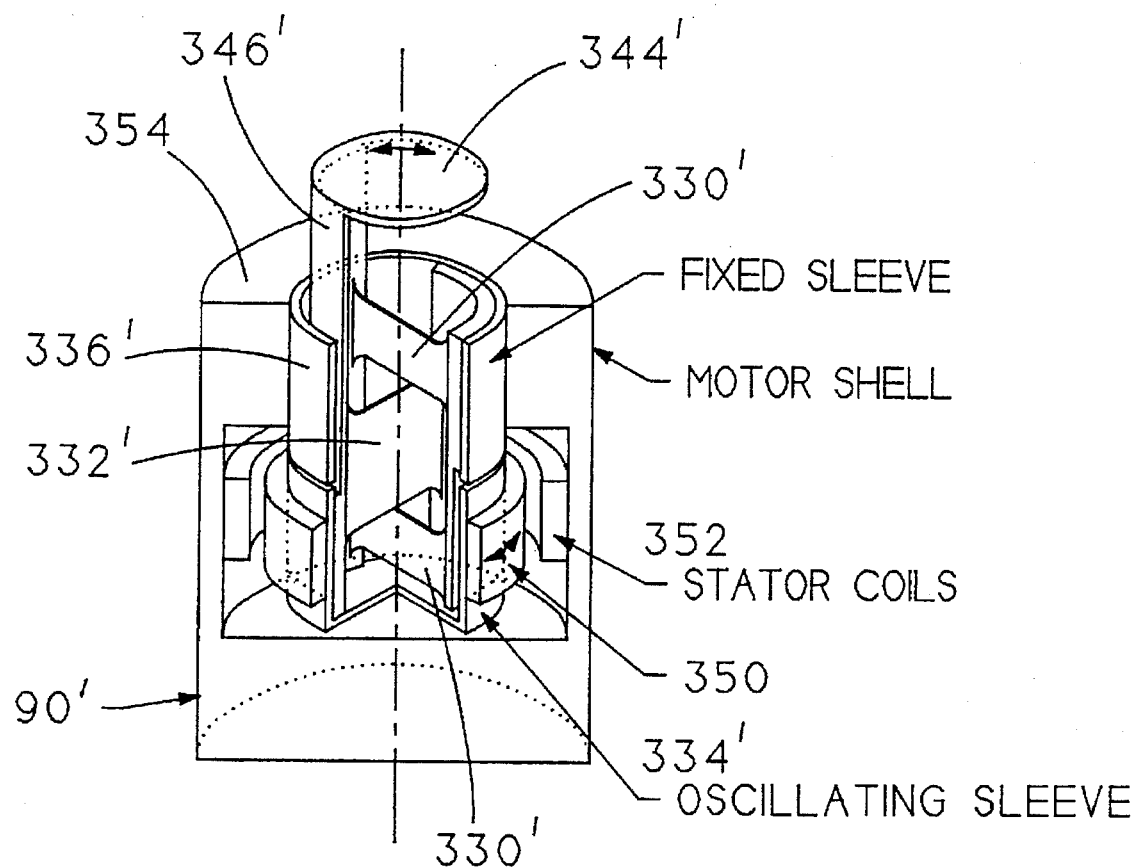

FIG. 13 shows another form of spring means operatively associated with motor 90' to assist the oscillatory motion of the motor. The spring means or flexual bearing means replaces the rotor assembly with the magnets mounted directly on the flexual bearing. The arrangement can be housed in the same actuator enclosure without adding any additional height to the overall assembly. As in the embodiment of FIG. 12, the flexual bearing means comprises flat, crossed springs 330', 332' supporting rotating sleeves 334', 336'. In this embodiment, however, one of the flexual bearing sleeves 334' has the motor rotor magnets 350 mounted thereto on the outer surface of sleeve 334' and facing the motor static coils 352. The other of the flexual bearing sleeves 336' is attached to the motor shell or housing 354. An output coupling in the form of disc 344' is connected by a member 346' to the movable bearing sleeve 334. Disc 344', in turn, would be fixed to the end of the probe arm which carries the transducer at the other end. The arrangement of FIG. 13 provides scan frequencies significantly greater than those obtained with the motor alone.

By way of example, in the illustrative embodiments of FIGS. 12 and 13 the flexual bearings comprising flat, crossed springs supporting rotating sleeves are commercially available from Lucas Aerospace Power Transmission Corp. under the designation Free-Flex Pivot frictionless bearing.

In the probe of FIGS. 1–8 in which both motor 90 and linear actuator operate in an oscillatory mode large amounts of energy are expended. Much of this energy is used in simply starting and stopping the motors 90, 92 themselves and only a fractional part of the energy is used in actually driving the transducer. In order to minimize much of the torque requirements of the motors and thereby minimize the energy consumed, it is proposed that a continuously rotating motor be used.

There are several advantages to the continuously rotating motor approach. Eliminating the need for high torque, oscillatory motion motors and replacing them with very low torque continuously rotating motors reduces the overall cost of the system. The RPM of the motor can be driven at very high speeds which will result in scan frequencies much higher than that attainable by the oscillatory approach. The large energy draw in starting and stopping the rotor of the actuator is virtually eliminated thus reducing the overall power consumption of the device. Oscillatory motion on ball bearings causes very high rates of wear. This will eventually result in bearing play which will cause the image quality to degrade. Using a continuously rotating approach will prevent the bearings from wearing out excessively early thereby improving overall reliability of the system.

Figure 14A:
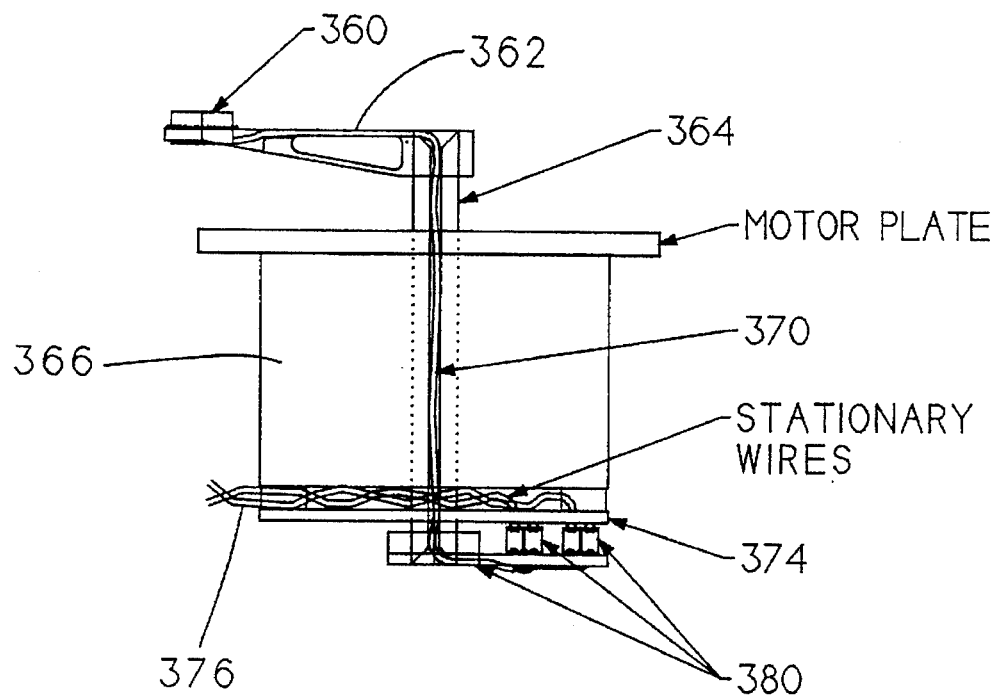

One type of architecture for implementing a continuously rotating scanner, i.e., a continuously rotating transducer is shown in FIG. 14A. A transducer 360 is mounted directly onto a flywheel 362 similar to arm 100 of FIG. 1 and is continuously rotated. The flywheel 362 is connected at the other end to the output shaft 364 of a motor 366. When the transducer 360 passes under the area of interest, data is collected. This approach is able to use a very low power low cost motor 366 for driving the flywheel transducer assembly. The only issue becomes one of how to couple the cable 370 of the ultrasonic transducer 360, which is continuously rotating, to the signal processor circuit card. There are several solutions for this problem, one of which is the use of commercially available slip rings. The stationary portion 372 of the slip ring can be mounted to the base 374 of the scanner where stationary wires 376 are attached and connected to the signal processor circuit card. The contact portion 380 of the slip rings can then be attached to the motor shaft 364 and wires 370 attached to it which lead to the transducer 360. In this manner, contact via the slip rings can be maintained to the signal processor while the motor 366 is rotating.

Figure 14B:
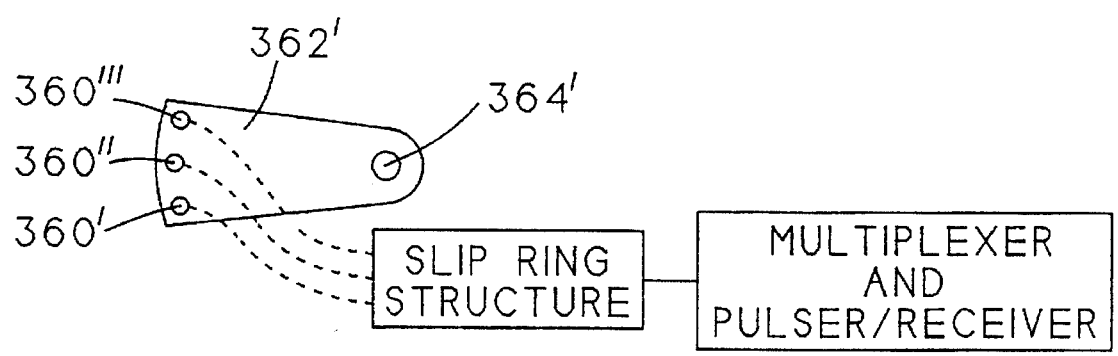

A variation on this approach could be made by adding multiple transducers 360', 360", 360'" around the perimeter of the flywheel 362'. The multiple transducers will reduce the amount of idle time while the transducer rotates around into position. Thus, adding a second transducer will reduce the scan time by 50%. A third transducer will reduce the original scan time by 66%, and so on. Implementing the multiple transducer approach will require some simple modifications to the system electronics. One modification could be to add a Signal Processor circuit board for every transducer that is added. This of course is an expensive approach but extremely easy to implement. Another approach would be to multiplex the front end portion of the pulser/receiver electronics and selectively pulse and receive echoes from each transducer. This would be the most cost effective solution. The foregoing is illustrated in FIG. 14b.

Figure 15:
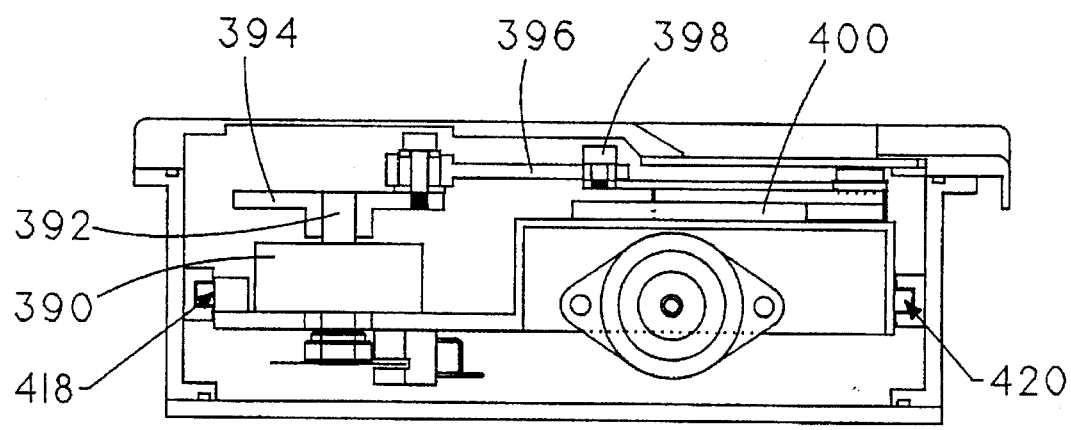
Figure 16:
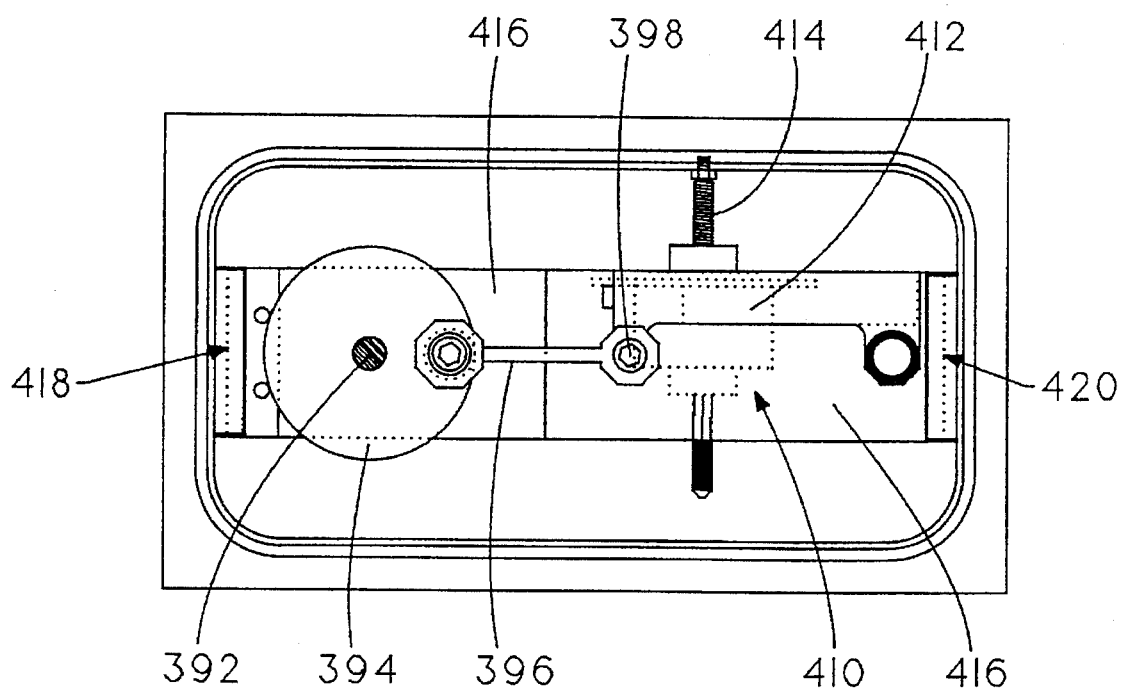

FIGS. 15 and 16 illustrate an alternative form of probe wherein scanning is performed linearly in both the X and Y directions. A continuously rotating motor 390 has an output shaft 392 connected to a flywheel 394 which in turn drives a pivoting arm 396. The pivoting arm 396 carries a transducer 398 at the other end which rides back and forth on a linear bearing support 400. As the motor 390 rotates, the pivot arm 396 drives the transducer 398 linearly back and forth along the path of the linear bearing 400. This is accomplished without reversing the motion of the motor 390 itself. Once the motor 390 is driven up to speed, the flywheel 394 overcomes the inertia of the motion of the transducer 398. The cable (not shown) connecting the transducer 398 to the signal processor simply has to flex in and out by the same amount as the linear motion of the movement of the transducer. Position feedback of the transducer can be accomplished by either attaching an optical encoder onto the motor shaft as previously done or by using a linear feedback device attached to the linear slide bearing 400. This device could be a sensor such as linear optical encoders, LVDT's, linear potentiometers, etc. The second axis of motion would then be accomplished in the same fashion as done in the probe of FIG. 1, i.e., by a linear actuator 410 comprising motor 412 and screw 414 which moves the entire structure 416 supported in the linear bearings 418, 420. Thus the arrangement of FIGS. 15 and 16 provides linear scanning movement of transducer 398 in mutually orthogonal directions, i.e., X and Y directions.

There can be applications requiring the probe 10 of FIGS. 1–11 to operate at low ambient temperature conditions. At least one temperature sensor such as a thermistor 430 can be located within cavity 28 for exposure to fluid 30 to monitor the temperature of the same. If desired another temperature sensor can be provided to monitor the ambient temperature. When thermistor 430 indicates that the temperature of fluid 30 is below a desired level, a control 436 signals microcontroller 302 to pulse energy through motor 90 rather than oscillating the motor. This pulsing of motor 90, i.e. simply applying the same polarity signals to the motor rather than reversing the polarity, has the effect of warming the fluid 30. This would be continued until thermistor 430 indicates that the temperature of fluid 30 has risen to the desired level.

Figure 17:
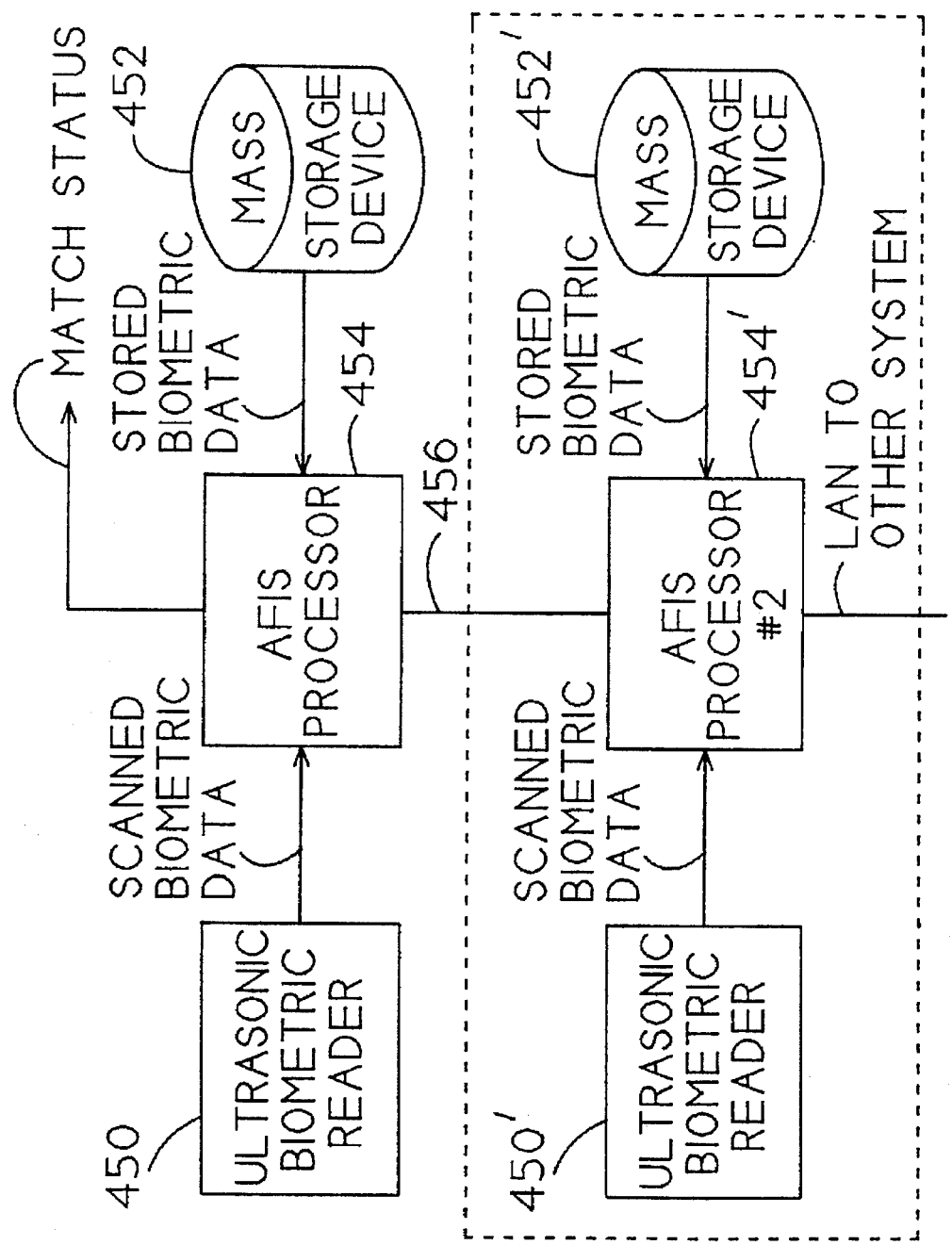
FIG. 17 is a block diagram illustrating the use of the scanner of the present invention in an identification system.

FIG. 17 illustrates the scanner of the present invention configured in an identification system which takes the image obtained from the scanned finger and compares it to a large database of previously scanned images to determine if a match exists. These identification systems, which typically are quite large and used by law enforcement agencies, immigration services and the like, have been generically termed AFIS or Automatic Fingerprint Identification Systems. Referring to FIG. 17 the ultrasonic biometric reader 450 comprises the scanner according to the present invention including probe assembly 10, signal processor 310, torque controller 300 and power supply/regulator 312, 314.

There is provided means in the form of mass storage device 452 for storing a database of previously stored images, i.e. stored fingerprint images. There is also provided a system processor means 454 having inputs coupled to database storage means 452 and to the output of the processor in ultrasonic biometric reader 450 for comparing a scanned image from reader 450 to the previously stored images in device 452 to determine if a match exists. FIG. 17 also illustrates a second combination of ultrasonic biometric reader 450', mass store device 452' and processor 454' with local, area network means 456 for connecting the processors 454 and 454' together.

Figure 18:
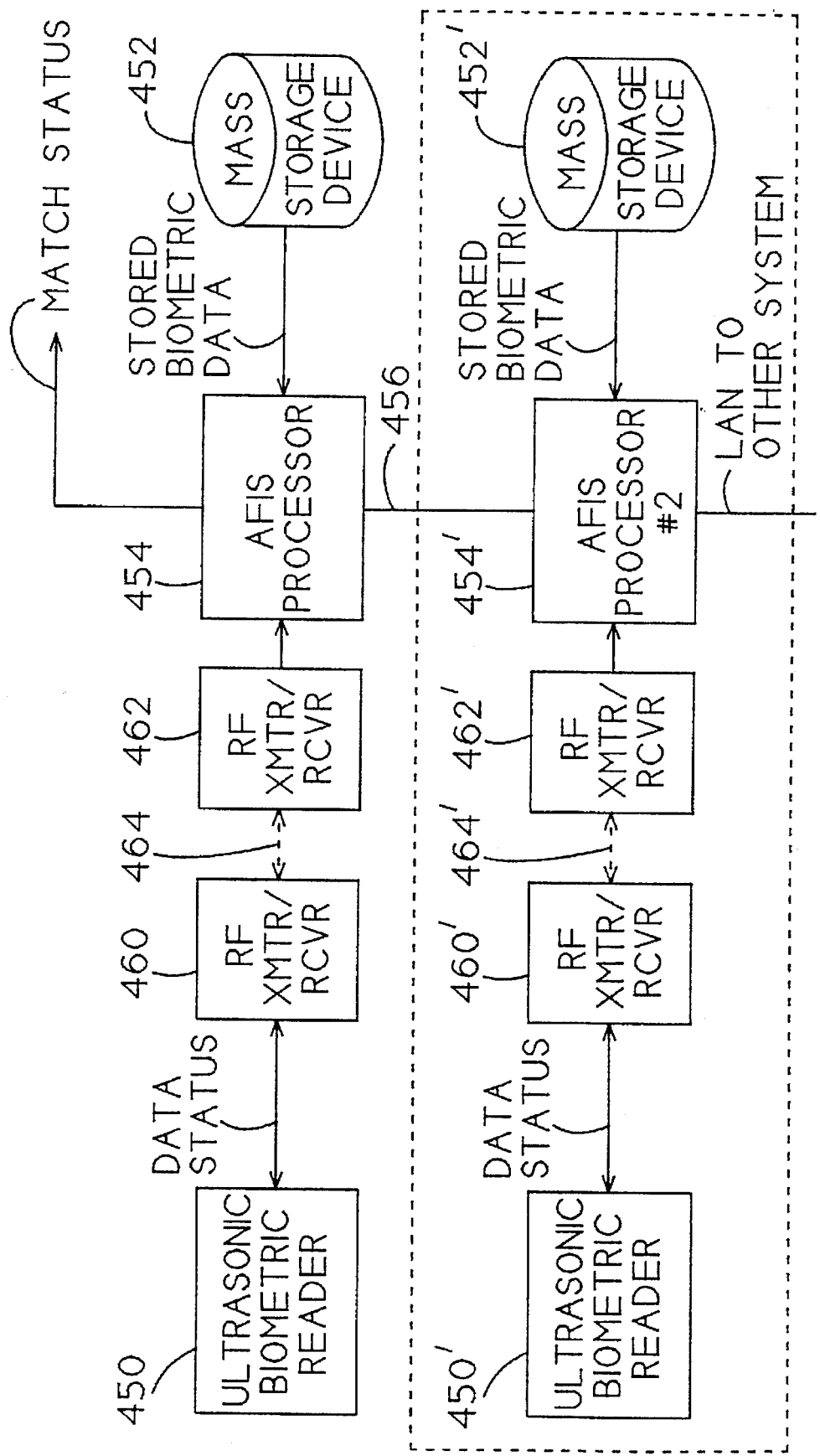
FIG. 18 is a block diagram of a wireless version of the system of FIG. 17.

FIG. 18 illustrates an alternative arrangement wherein the hard-wired communication link between ultrasonic biometric reader 450 and processor 454 is replaced by a wireless communication link such as an RF transmitter/receiver 460 connected to the output of biometric reader 450, an RF transmitter/receiver 462 connected to the input of processor 454 and the transmission medium 454 therebetween. As a result, the ultrasonic biometric reader 450 can be located in a remote or mobile area such as a police car or other remote data entry site. A finger is placed on the reader, scanned and the data transmitted in a wireless manner to an AFIS processor for processing. The communication link is bi-directional and transmits back to the reader any pertinent information. Other wireless communication links can be employed such as optical, ultrasonic and the like.

Figure 19:
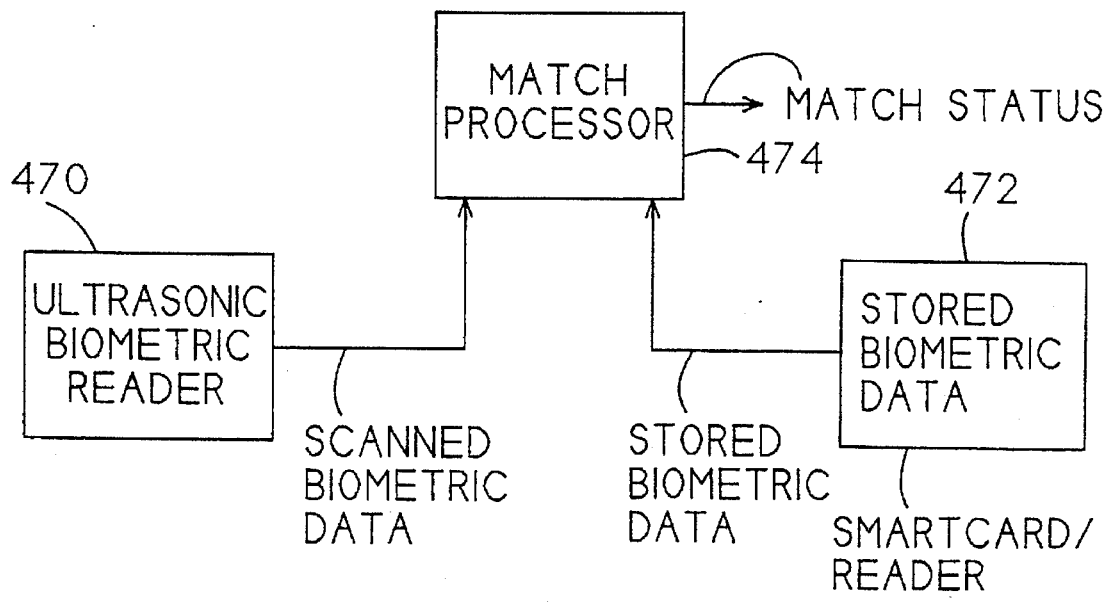
FIGS. 19 and 20 are block diagrams illustrating the use of the scanner of the present invention in a verification system.
Figure 20:
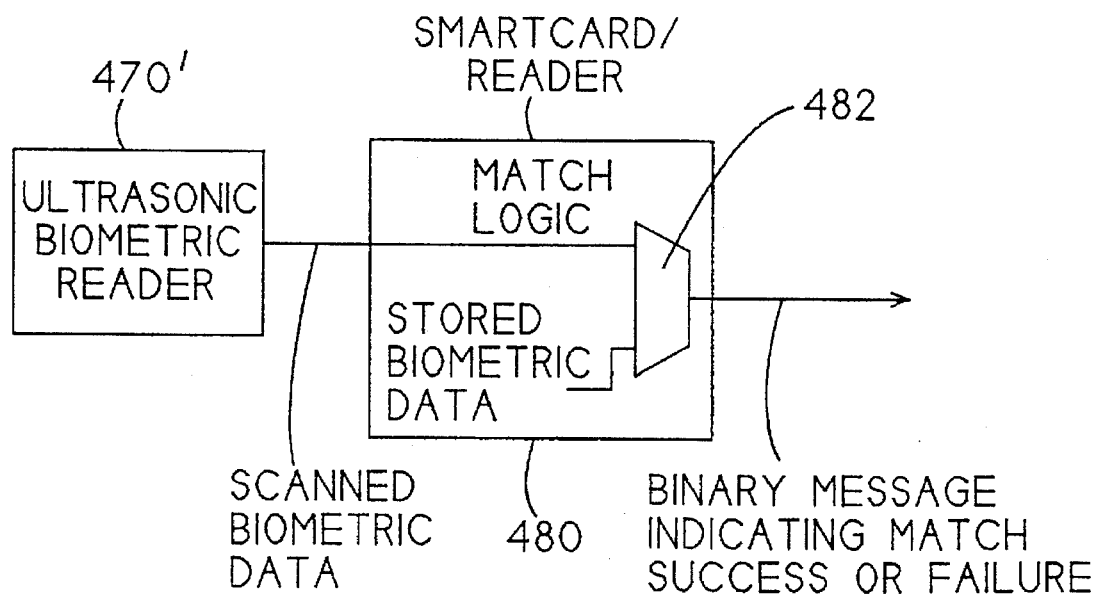

FIGS. 19 and 20 illustrate the scanner of the present invention configured in a verification system where a finger is scanned and compared to a single reference print to verify if the individual is who he claims to be. This type of system is much less complex in nature as compared to identification systems since it does not require the extensive searching that larger AFIS system must do, which require high speed processors, large databases, etc. One method of implementing such a system is using smartcards or any other type of portable data storage device such as a mag-stripe card, optical storage card, semiconductor storage card and the like. Smartcards are plastic cards similar in size to a standard credit card for carrying by persons. The traditional magstripe found on the back of the card is either replaced or supplemented by an on board microprocessor. The microprocessor has built in memory which enables two options for overall system configuration. A first option is to simply encode the biometric data into the memory of the smartcard. A person wishing to have his identity verified places his finger on the ultrasonic reader and the finger is scanned. The data is then read out of the smartcard presented by the individual and a computer is used to compare the two images. This is illustrated in FIG. 19 wherein an ultrasonic biometric reader 470 comprises the system according to the present invention including probe assembly 10, signal processor 310, torque controller 300 and power supply regulator 312, 314. A record member 472 in the form of the smartcard mentioned above has storage means containing a recorded biometric image, i.e. for storing a recorded fingerprint image. A processor means 474 has a first input for receiving output signals from the ultrasonic biometric reader and a second input for receiving a signal representation of the recorded image to determine if a match exists between the scanned and recorded images. Thus, in the arrangement of FIG. 19 the record member 472 and processor 474 are physically separate.

A second option is similar to the first option with the main difference being that the computer used to compare the two images is replaced by the processor of the smartcard. Thus, the smartcard not only contains the biometric data of the finger but is also responsible for comparing that data to the scanned data of the finger. This is illustrated in FIG. 20 wherein a smartcard or record member 480 has storage means containing a recorded biometric image and processor means 482 thereon having one input for receiving output signals from the ultrasonic biometric reader 470' and a second input for receiving a signal representation of the recorded image to determine if a match exists between the scanned and recorded images. Thus, in the arrangement of FIG. 18 the record member 480 and the processor 482 are physically integrated.

Figure 21:
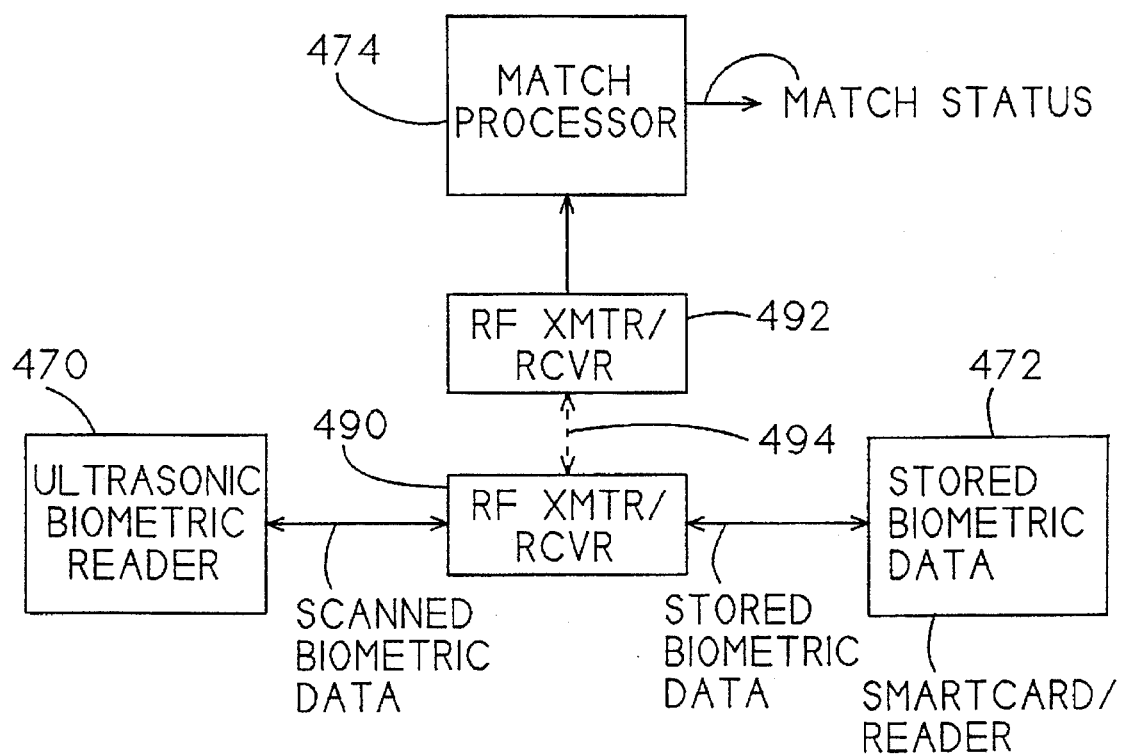
FIG. 21 is a block diagram illustrating a wireless version of the system of FIG. 20.

FIG. 21 illustrates an alternative arrangement wherein the hard-wired communication link between processor 474 and ultrasonic biometric reader 470 and record member 472 in the arrangement of FIG. 19 is replaced by a wireless communication link. The wireless communication link comprises an RF transmitter/receiver 490 connected to the outputs of biometric reader 470 and record member 472, an RF transmitter/receiver 402 connected to processor 474 and the transmission medium therebetween. The RF communication link is bidirectional, allowing match results to be sent back to the reader subsystem. Other wireless communication links can be employed such as optical, ultrasonic and the like.

It is therefore apparent that the present invention accomplishes its intended object. While embodiments of the present invention have been described in detail, that is for the purpose of illustrations, not limitation.

What is claimed is:

1. A probe for an ultrasonic imaging system for providing an output ultrasonic beam to scan human or animal tissue having a surface, said probe comprising:
    a) means for defining said surface in a manner supporting said human or animal tissue for imaging the same;
    b) transducer means for providing an output ultrasonic beam;
    c) electrically-operated motive means operatively coupled to said transducer means for moving said transducer means in a manner such that said output ultrasonic beam is directed in a path along said surface;
    d) fluid-tight housing means extending from said surface defining means and having an interior region containing said transducer means and said motive means; and
    e) a fluid filling said interior region of said housing means, said fluid having an acoustic impedance substantially equal to that of water and having a viscosity sufficiently low so as not to impede the movement of said transducer means and being electrically non-conductive; and
    f) arm means for directly coupling said motive means to said transducer means, said arm means having sufficient rigidity so as not to bend or flex during movement of said motive means and said arm means having a structure which minimizes drag as said arm means moves through said fluid.

2. A probe according to claim 1, wherein said fluid comprises mineral oil.

3. A probe according to claim 1, wherein said motive means comprises:
    a) motor means having an output shaft for providing oscillatory output motion;
    b) means for coupling said output shaft to said transducer means so that in response to oscillation of said shaft said output ultrasonic beam is directed in an arcuate path along said surface; and
    c) means for moving said transducer means in a manner such that said output ultrasonic beam is directed in a linear path along said surface and in a radial direction relative to said arcuate path.

4. A probe according to claim 1, wherein said means for defining said surface comprises platen means of a material having an acoustic impedance substantially matching the acoustic impedance of the tissue being imaged.

5. A probe according to claim 1, wherein said platen means comprises a first section permanently sealed to said housing means and a second section defining said surface and removable from said first section for replacement.

6. A probe according to claim 1, wherein said means for defining said surface comprises platen means in the form of a body of material having an acoustic impedance substantially matching the acoustic impedance of the tissue being imaged and having sufficient mechanical strength to support the tissue without deflection or deformation.

7. A probe according to claim 6, further including a coating on said body of a material which improves mechanical coupling of said body to the tissue being imaged while maintaining the matching of acoustic impedance.

8. A probe according to claim 1, wherein said transducer means is operatively coupled to said motive means by means for positioning said transducer means closely adjacent said supporting means in a manner directing said ultrasonic beam on said surface and so that the size of said beam at its focal point is as small as possible to maximize the resolution of said system.

9. A probe according to claim 1, further including hermetic seal means in said housing and electrical conductor means extending from said motive means through said seal means.

10. A probe according to claim 1, further including means operatively associated with said housing for accommodating thermal expansion and contraction of said fluid.

11. A probe according to claim 1, further including sensing means in said interior region of said housing for monitoring the temperature of said fluid.

12. A probe according to claim 11, further including means operatively connected to said sensing means for heating said fluid when said sensing means indicates that the temperature of said fluid is below a predetermined level.

13. A probe for an ultrasonic imaging system for providing an output ultrasonic beam to scan human or animal tissue having a surface, said probe comprising:
a) means for defining said surface in a manner supporting said human or animal tissue for imaging the same;
b) transducer means for providing an output ultrasonic beam;
c) motor means having an output shaft for providing oscillatory output motion, said output shaft having a longitudinal axis;
d) means for coupling said output shaft to said transducer means so that in response to oscillation of said shaft said output ultrasonic beam is directed in a path along said surface, said means for coupling comprising arm means extending in a direction substantially perpendicular to said longitudinal axis of said motor output shaft and said arm means comprising a pair of arm sections spaced apart in a direction substantially parallel to said shaft longitudinal axis so that said arm means has sufficient rigidity so as not to bend or flex during oscillation of said shaft.

14. A probe according to claim 13, further including
a) fluid-tight housing means extending from said surface defining means and having an interior region containing said transducer means, said motor means and said arm means;
b) a fluid filling said interior region of said housing means, said fluid having an acoustic impedance substantially equal to that of water and having a viscosity sufficiently low so as not to impede the movement of said transducer means and being electrically non-conductive; and
c) said arm sections having surfaces disposed in planes substantially parallel to said longitudinal axis of said motor shaft, said surfaces having a sufficiently small area so as to minimize drag as said arm means moves through said fluid.

15. A probe according to claim 13, wherein said means for defining said surface comprises platen means of a material having an acoustic impedance substantially matching the acoustic impedance of the tissue being imaged.

16. A probe according to claim 13, wherein said means for defining said surface comprises platen means in the form of a body of material having an acoustic impedance substantially matching the acoustic impedance of the tissue being imaged and having sufficient mechanical strength to support the tissue without deflection or deformation.

17. A probe according to claim 16, further including a coating on said body of a material which improves mechanical coupling of said body to the tissue being imaged while maintaining the matching of acoustic impedance.

18. A probe according to claim 13, wherein said arm means moves said transducer means along an arcuate path and further including means for moving said transducer means in a manner such that said output ultrasonic beam is directed in a linear path along said surface and in a radial direction relative to said arcuate path.

19. A probe according to claim 13, further including position feedback means mounted on said output shaft of said motor means between said motor means and said arm means.

20. A probe according to claim 13, wherein said arm means positions said transducer means closely adjacent said supporting means in a manner directing said ultrasonic beam on said surface and so that the size of said beam at its focal point is as small as possible to maximize the resolution of said system.

21. A probe for an ultrasonic imaging system for providing an output ultrasonic beam to scan human or animal tissue having a surface, said probe comprising:
a) means for defining said surface in a manner supporting said human or animal tissue for imaging the same;
b) transducer means for providing an output ultrasonic beam;
c) electrically-operated motive means operatively coupled to said transducer means for moving said transducer means in a manner such that said output ultrasonic beam is directed in a path along said surface;
d) fluid-tight housing means extending from said surface defining means and having an interior region containing said transducer means and said motive means;
e) a fluid filling said interior region of said housing means, said fluid having an acoustic impedance substantially equal to that of water and having a viscosity sufficiently low so as not to impede the movement of said transducer means;
f) expansion bellows means operatively associated with said housing for accommodating thermal expansion and contraction of said fluid; and
g) said housing having an end wall and said expansion bellows means being located in a chamber extending from said end wall, said expansion bellows means comprising a substantially cup-shaped diaphragm of flexible material compatible with said fluid.

22. A probe according to claim 21, wherein said expansion bellows means has a size sufficient to accommodate total thermal expansion experienced by said fluid within a selected temperature range.

23. A probe for an ultrasonic imaging system for providing an output ultrasonic beam to scan human or animal tissue having a surface, said probe comprising:
 a) means for defining said surface in a manner supporting said human or animal tissue for imaging the same;
 b) transducer means for providing an output ultrasonic beam;
 c) motor means having an output shaft for providing continuous rotary output motion;
 d) flywheel means for coupling said output shaft to said transducer means so that in response to rotation of said shaft said output ultrasonic beam is directed in a path along said surface; and
 e) commutator means operatively associated with said motor shaft for making electrical connection between said transducer means and an external circuit.

24. A probe for an ultrasonic imaging system for providing an output ultrasonic beam to scan human or animal tissue having a surface, said probe comprising:
 a) means for defining said surface in a manner supporting said human or animal tissue for imaging the same;
 b) transducer means for providing an output ultrasonic beam;
 c) motor means having an output shaft for providing continuous rotary output motion;
 d) motion conversion means for coupling said output shaft to said transducer means so that in response to rotation of said shaft said transducer is reciprocated to direct said ultrasonic beam in a first linear path along said surface; and
 e) means for moving said transducer means in a manner such that said output ultrasonic beam is directed in a second linear path along said surface substantially orthogonal to said first linear path.

25. A biometric identification system comprising:
 a) an ultrasonic imaging system for imaging human or animal tissue having a surface and comprising probe means including means for defining said surface in a manner supporting said human or animal tissue for imaging the same, transducer means for providing an output ultrasonic beam; electrically-operated motive means operatively coupled to said transducer means for moving said transducer means in a manner such that said output ultrasonic beam is directed in a path along said surface; fluid-tight housing means extending from said surface defining means and having an interior region containing said transducer means and said motive means; and a fluid filling said interior region of said housing means, said fluid having an acoustic impedance substantially equal to that of water and having a viscosity sufficiently low so as not to impede the movement of said transducer means and being electrically non-conductive;
 b) said imaging system further comprising torque controller means operatively connected to said probe means for controlling said motive means to provide said scan of said surface and signal processor means operatively connected to said probe means for receiving signals produced in response to said scan of said surface and for processing said signals to provide an output;
 c) means for storing a database of previously stored images; and
 d) system processor means having inputs coupled to said database storage means and to the output of said processor means for comparing a scanned image from said ultrasonic image system to the previously stored images in said database storage means to determine if a match exists.

26. A biometric verification system comprising:
 a) an ultrasonic imaging system for imaging human or animal tissue having a surface and providing output signals representing a scanned biometric image;
 b) said ultrasonic imaging system comprising probe means including means for defining said surface in a manner supporting said human or animal tissue for imaging the same, transducer means for providing an output ultrasonic beam; electrically-operated motive means directly and ridgidly coupled to said transducer means for moving said transducer means in a manner such that said output ultrasonic beam is directed in a path along said surface; fluid-tight housing means extending from said surface defining means and having an interior region containing said transducer means and said motive means; and a fluid filling said interior region of said housing means, said fluid having an acoustic impedance substantially equal to that of water and having a viscosity sufficiently low so as not to impede the movement of said transducer means and being electrically non-conductive;
 c) a record member having storage means containing a recorded biometric image; and
 d) processor means having a first input for receiving output signals from said ultrasonic imaging system and a second input for receiving a signal representation of said recorded image to determine if a match exists between said scanned and recorded images.

27. A probe for an ultrasonic imaging system for providing an output ultrasonic beam to scan human or animal tissue having a surface, said probe comprising:
 a) means for defining said surface in a manner supporting said human or animal tissue for imaging the same;
 b) transducer means for providing an output ultrasonic beam;
 c) electrically-operated motive means operatively coupled to said transducer means for moving said transducer means in a manner such that said output ultrasonic beam is directed in a path along said surface;
 d) fluid-tight housing means extending from said surface defining means and having an interior region containing said transducer means and said motive means;
 e) a fluid filling said interior region of said housing means, said fluid having an acoustic impedance substantially equal to that of water and having a viscosity sufficiently low so as not to impede the movement of said transducer means and being electrically nonconductive;
 f) said motive means comprising motor means having an output shaft for providing oscillatory output motion, means for coupling said output shaft to said transducer means so that in response to oscillation of said shaft said output ultrasonic beam is directed in an arcuate path along said surface, and means for moving said transducer means in a manner such that said output ultrasonic beam is directed in a linear path along said surface and in a radial direction relative to said arcuate path; and g) encoder means mounted on said output shaft of said motor means between said motor means and said coupling means.

28. A probe for an ultrasonic imaging system for providing an output ultrasonic beam to scan human or animal tissue having a surface, said probe comprising:

a) means for defining said surface in a manner supporting said human or animal tissue for imaging the same;

b) transducer means for providing an output ultrasonic beam;

c) electrically-operated motor means having an output shaft operatively connected by coupling means to said transducer means for moving said transducer means in a manner such that said output ultrasonic beam is directed in a path along said surface;

d) fluid-tight housing means extending from said surface defining means and having an interior region containing said transducer means and said motive means;

e) a fluid filling said interior region of said housing means, said fluid having an acoustic impedance substantially equal to that of water and having a viscosity sufficiently low so as not to impede the movement of said transducer means and being electrically non-conductive; and f) encoder means mounted on said output shaft of said motor means between said motor means and said coupling means.

29. A probe for an ultrasonic imaging system for providing an output ultrasonic beam to scan human or animal tissue having a surface, said probe comprising:

a) means for defining said surface in a manner supporting said human or animal tissue for imaging the same;

b) transducer means for providing an output ultrasonic beam;

c) electrically-operated motive means operatively coupled to said transducer means for moving said transducer means in a manner such that said output ultrasonic beam is directed in a path along said surface;

d) fluid-tight housing means extending from said surface defining means and having an interior region containing said transducer means and said motive means;

e) a fluid filling said interior region of said housing means, said fluid having an acoustic impedance substantially equal to that of water and having a viscosity sufficiently low so as not to impede the movement of said transducer means and being electrically non-conductive;

f) sensing means in said interior region of said housing for monitoring the temperature of said fluid; and g) control means operatively connected to said sensing means and to said electrically operated motive means for supplying electrical power to said motive means in a manner causing said motive means to release heat to said fluid when said sensing means indicates that the temperature of said fluid is below a predetermined level.

\* \* \* \* \*